United States Patent
Hall et al.

(10) Patent No.: US 11,619,610 B2
(45) Date of Patent: Apr. 4, 2023

(54) COMPUTER-IMPLEMENTED PROCESSING FOR NON-DESTRUCTIVE EVALUATION OF WOODEN SPECIMEN

(71) Applicant: VOLT HOLDINGS LIMITED, Auckland (NZ)

(72) Inventors: Wayne Hall, Denver, CO (US); Dion Hall, Canberra (AU); Yishi Lee, Littleton, CO (US)

(73) Assignee: VOLT HOLDINGS LIMITED, Auckland (NZ)

( * ) Notice: Subject to any disclaimer, the term of this patent is extended or adjusted under 35 U.S.C. 154(b) by 901 days.

(21) Appl. No.: 16/532,264

(22) Filed: Aug. 5, 2019

(65) Prior Publication Data

US 2021/0041397 A1  Feb. 11, 2021

(51) Int. Cl.
   *G01N 33/46*  (2006.01)
   *G01N 29/04*  (2006.01)
   (Continued)

(52) U.S. Cl.
   CPC ............ *G01N 29/04* (2013.01); *G01N 33/46* (2013.01); *G06F 3/0482* (2013.01); *G06K 9/6232* (2013.01)

(58) Field of Classification Search
   CPC .................. G01N 29/04; G01N 33/46; G01N 2291/02845; G01N 29/07; G01N 29/11; G01N 29/2481; G01N 2291/0238; G01N 29/12; G01N 29/14; G01N 19/22; G01N 29/34; G01N 29/44; G01N 2291/0258; G06F 3/0482; G06K 9/6232; G06K 9/0053; G06K 9/00543; G06N 3/02; G06N 20/00
   (Continued)

(56) References Cited

U.S. PATENT DOCUMENTS 11,324,210 B2 *  5/2022  Ben Hamozeg ... G01N 29/4427
2008/0127793 A1   6/2008  Ikeda
(Continued)

FOREIGN PATENT DOCUMENTS

| CN | 107144635 | * | 9/2017 |
| WO | 2016075641 A1 | | 5/2016 |
| WO | 2016120774 A1 | | 8/2016 |

*Primary Examiner* — Robert R Raevis

(57) ABSTRACT

Non-limiting examples of the present disclosure describe a non-destructive evaluation (NDE) application/service that is configured for NDE of a wooden specimen. The NDE application/service provides a user-friendly graphical user interface that enables inspectors to manage each phase of NDE of a wooden specimen through one or more computing devices. An exemplary NDE application/service is configured to analyze captured acoustic signal data (e.g., ultrasonic signal data) and transform that captured signal data into feature information that is used to more accurately assess the structural integrity of a wooden specimen. For instance, execution of a programmed NDE application/service employs a trained artificial intelligence (AI) classifier that evaluates waveform propagation (e.g., TOF and energy attenuation) through a wooden specimen to classify a condition and a quality the wooden specimen. An NDE report may be generated that provides an inspector with an assessment of the wooden specimen and/or a network of wooden specimen.

21 Claims, 20 Drawing Sheets

(51) Int. Cl.
*G06F 3/0482* (2013.01)
*G06K 9/62* (2022.01)

(58) Field of Classification Search
USPC ........ 73/1.01, 573, 579, 594, 597, 598, 599,
73/600, 78, 866, 865.8; 702/33–35, 85,
702/105
See application file for complete search history.

(56) References Cited

U.S. PATENT DOCUMENTS

| | | |
|---|---|---|
| 2008/0197054 A1 | 8/2008 | Lindstrom |
| 2014/0069192 A1 | 3/2014 | Bartuli et al. |

\* cited by examiner

UB1000 Test Controller. Rev 20190508

| Cal Test |  Enter Pole ID: _____

Enter Height of Test AGL (inch): _____

Notes: __Test No. 1__   Metric (M)/ Imperial (I): __I__   Other notes: _____

| Measure Battery Levels | Initial Scan 7 Point Test | Eight Probe 28 Point Test |

Probe A/45        21%
Probe B/225       -1%
JBL Flip 4
Unknown device
Unknown device
Unknown device
Unknown device

1100

↓

1200 →

1300 →

1400

1500

1600

1700

1800 →

COMPUTER-IMPLEMENTED PROCESSING FOR NON-DESTRUCTIVE EVALUATION OF WOODEN SPECIMEN

TECHNICAL FIELD

The present disclosure relates to devices, systems and methods capable of producing and receiving acoustic signals in the area of non-destructive evaluation (NDE), where the acoustic signals may be utilized to assess structural integrity of a wood specimen, among other types of analysis.

BACKGROUND

The aging infrastructure power distribution grids across the world demands a rigorous and an objective monitoring process to assess structural integrity of hundreds of millions of wooden utility poles. Current inspection methodologies are antiquated and either lack the ability to provide truly accurate evaluations and/or result in compromising the structural integrity of a utility pole. For instance, one commonly utilized method of evaluating utility poles is an inspectors' visual evaluation of the pole. Visual inspection may be able to identify some structural integrity issues but is not a true indicator of whether the utility pole is experiencing incipient decay internally. As an example, a utility pole may appear to be fine, where an inspector gives the utility pole a passing grade, but internal decay may significantly affect the longevity of the pole, sometimes cutting its lifetime by decades. As there may be long gaps between the times when a utility pole is inspected, it is paramount to accurately assess the structural integrity of the utility pole.

Alternative measures for inspecting utility poles include drilling into the utility pole and testing a wood sample from its core. While this may provide more a reliable indication of whether a utility pole is experiencing decay, as compared with visual inspection, drilling into the core of a utility pole compromises the structural integrity of the pole. For instance, utility poles are coated with a protective layering that helps minimize exposure to elements that expedite decay. If this protective layering is compromised, decay can be expedited due to exposure to elements of nature, bacteria, etc.

Additional concerns exist when new technology is integrated in a field that commonly uses such antiquated methods to evaluate structural integrity. For instance, usage of complex electronic equipment may pose training challenges for inspectors and result in human error during actual operation as complex operating environments can be created. Additionally, signal data that may be initially collected during an inspection does not directly translate into meaningful information that an inspector can utilize to truly assess the structural integrity of a wooden specimen. Technical challenges are posed when contemplating how to decode waveforms of signal data in order to obtain important parameters for interpreting a physical structure of a specimen. As such, inspectors often rely on subjective assessment of the structural integrity by an inspector, thereby decreasing the likelihood of an accurate assessment. In most technical instances, inspectors are not trained to analyze signal data. This makes it it nearly impossible to obtain real-time (or near real-time) assessments regarding condition a single wooden specimen let alone a network of wooden specimen.

For these and other reasons, the present disclosure is presented to greatly advance the technical field of testing of structural integrity of wooden specimen including wooden utility poles.

SUMMARY

In view of the foregoing technical challenges, non-limiting examples of the present disclosure describe an NDE application/service that is configured for NDE of a wooden specimen. A non-limiting example of a wooden specimen is a wooden utility pole. However, examples described herein may pertain to NDE of any type of wooden specimen including but not limited to wooden cylinders such as wooden utility poles, pilings and logs, among other examples. It is to be further understood that the present disclosure may be extended to work with structures comprising any material (not just wood) though modifications that are recognized by one skilled in the field of art. The NDE application/service provides a user-friendly graphical user interface that enables inspectors to manage each phase of NDE of a wooden specimen through one or more computing devices. Non-limiting examples of phases of NDE comprise are not limited to: NDE device configuration; signal feasibility testing; wooden specimen health analysis (e.g., condition, quality and/or strength/remaining strength of a wooden specimen); network health analysis and forecasting (e.g., for a plurality of wooden specimen); and generation and presentation of NDE reports, among other examples.

An exemplary NDE application/service is configured to analyze captured acoustic signal data (e.g., ultrasonic signal data) and transform that captured signal data into feature information that is used to more accurately assess the structural integrity (e.g., condition and quality) of a specimen (e.g., wooden specimen). Analysis of acoustic signal data (i.e. waveforms thereof) combines time of flight (TOF) and energy attenuation information (e.g., peak energy of a waveform) to qualitatively and quantitively determine mechanical moduli that are directly related to a structural integrity of a wooden specimen. For instance, execution of a programmed NDE application/service employs a trained artificial intelligence (AI) classifier that evaluates waveform propagation (e.g., TOF and energy attenuation) through a wooden specimen to classify condition and quality of the wooden specimen. A classification of a structural integrity of a wooden specimen may be included in an NDE report that is generated and surfaced, for example, through the graphical user interface of the NDE application/service or an application/service that is associated with a selected format of the NDE report as identified in the graphical user interface. In further examples, the trained AI classifier may be further configured to contemplate other factors associated with a wooden specimen such as load conditions, environmental conditions, physical conditions, etc. This enables a more comprehensive NDE report to be generated that may pertain to the state of a wooden specimen and/or a network of wooden specimen. That is, an NDE report may reflect a present state of one or more wooden specimen, a projected future state of one or more wooden specimen or a combination thereof.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIGS. 10-18 illustrate processing device views of an NDE application/service usable to conduct NDE of a wooden specimen, with which aspects of the present disclosure may be practiced.

DETAILED DESCRIPTION

Figure 1:
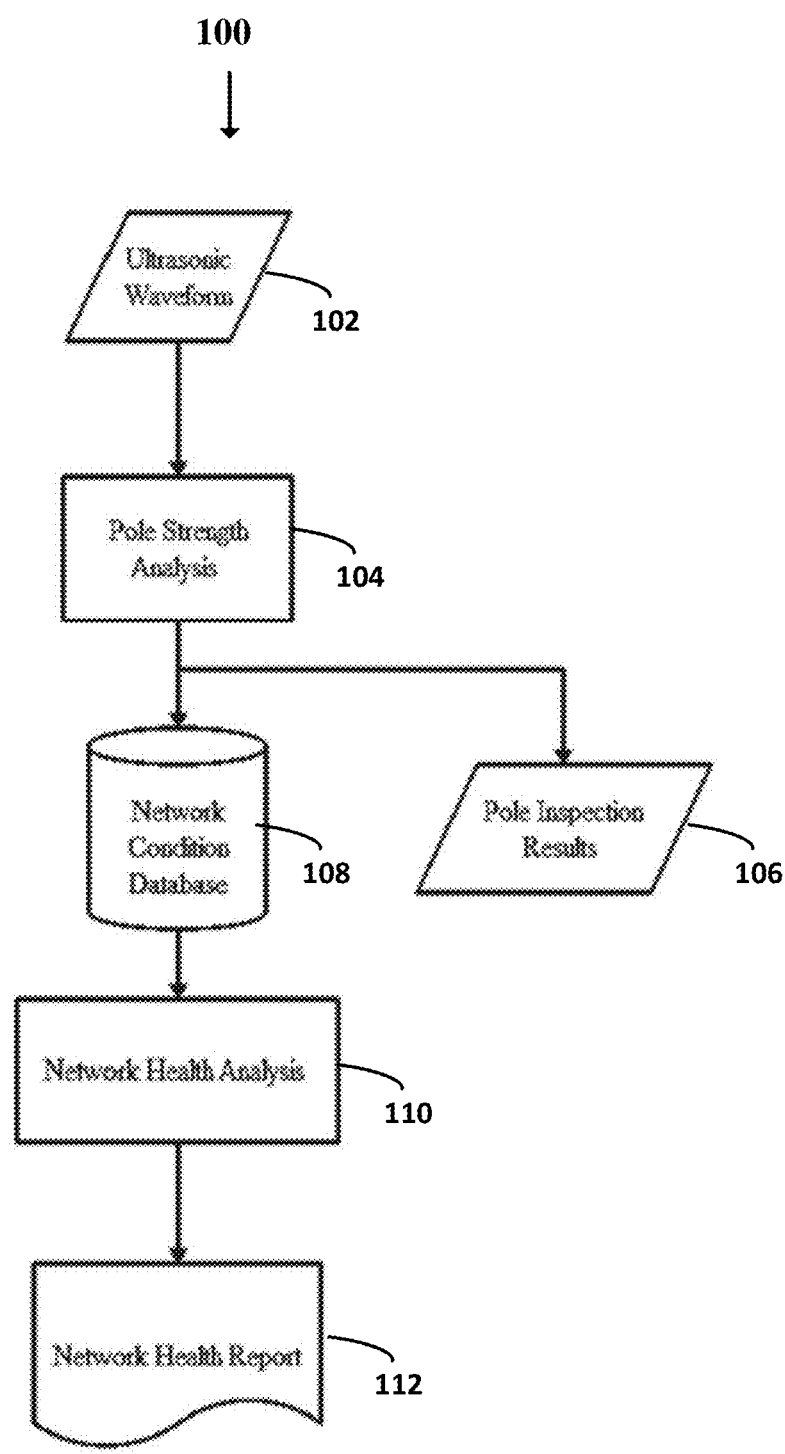
FIG. 1 illustrates flow diagram of analysis executed by a non-destructive evaluation (NDE) application/service for evaluating wooden specimen, with which aspects of the present disclosure may be practiced.

Non-limiting examples of the present disclosure describe an NDE application/service that is configured for NDE of a wooden specimen. A non-limiting example of a wooden specimen is a wooden utility pole. However, examples described herein may pertain to NDE of any type of wooden specimen including but not limited to wooden cylinders such as wooden utility poles, pilings and logs, among other examples. It is to be further understood that the present disclosure may be extended to work with structures comprising any material (not just wood) though modifications that are recognized by one skilled in the field of art. The NDE application/service provides a user-friendly graphical user interface (GUI) that enables inspectors to manage each phase of NDE of a wooden specimen through one or more computing devices. Non-limiting examples of phases of NDE comprise are not limited to: NDE device configuration; signal feasibility testing; wooden specimen health analysis (e.g., condition, quality and/or strength/remaining strength of a wooden specimen); network health analysis and forecasting (e.g., for a plurality of wooden specimen); and generation and presentation of NDE reports, among other examples.

An exemplary NDE application/service is configured to analyze captured acoustic signal data (e.g., ultrasonic signal data) and transform that captured signal data into feature information that is used to accurately assess the structural integrity (e.g., condition and quality) of a specimen (e.g., wooden specimen). Analysis of acoustic signal data (i.e. waveforms thereof) combines time of flight (TOF) and energy attenuation information (e.g., peak energy of a waveform) to quantitatively and qualitatively determine mechanical moduli that are directly related to structural integrity. For instance, execution of a programmed NDE application/service employs a trained (data-driven) artificial intelligence (AI) classifier that evaluates waveform propagation (e.g., TOF and energy attenuation) through a wooden specimen to classify condition and quality of the wooden specimen. A classification of a structural integrity of a wooden specimen may be included in an NDE report that is generated and surfaced through the GUI of the NDE application/service or an application/service that is associated with a selected format of the NDE report as identified in the GUI. In further examples, the trained AI classifier may be further configured to contemplate other factors associated with a wooden specimen such as load conditions, environmental conditions, physical conditions, etc. This enables a more comprehensive and accurate NDE report to be generated that may pertain to the state of a wooden specimen and/or a network of wooden specimen. That is, an NDE report may reflect a present state of one or more wooden specimen, a projected future state of one or more wooden specimen or a combination thereof.

One non-limiting example of the present disclosure relates to operations for NDE of a wooden specimen that may be executed at one or more computing devices, for example, that are executing an exemplary NDE application/service. Acoustic signal data may be received at a computing device, where the acoustic signal data related to NDE of a wooden specimen (e.g., ultrasonic signal data is transmitted through a wooden specimen). Trained data modeling may be applied to analyze waveforms of the received acoustic signal(s). For instance, analysis of waveforms of a received acoustic signal may comprise extracting data features related to arrival regions of said waveforms, where extracted features of a transmitted waveform may correspond with one or more regions of a wooden specimen. Extracted data features may comprise waveform data from captured acoustic signal data, specifically TOF and energy attenuation data (e.g., peak energy) of different arrival waveforms. Each arrival waveform is correlated with a specific region of a wooden specimen. Based on the extracted features, supervised or unsupervised learning may be applied by using labeled data from a model to configure the classifier. Based on different training data reflecting varying levels of structural integrity (e.g., condition and/or quality), a trained classifier can be used to accurately evaluate the conditions in various regions of the wooden specimen. An NDE report of the wooden specimen may be generated and subsequently presented through a GUI that is executing on the computing device. The graphical user interface may be a GUI of NDE application/service. As referenced in the foregoing description, an NDE report comprises a classification of structural integrity of the wooden specimen based on a result of execution of the data modeling.

In further examples, applied physics combined with data modeling enables an AI classifier to utilize the extracted features to evaluate other aspects of structural integrity of a wooden specimen such as quality of a wooden specimen (e.g., wood that behaving normally/in good shape versus compromised wood). For example, a determined quality of the wooden specimen may be utilized to further determine a strength of the wooden specimen as well as determine present value and forecast future projections for the wooden specimen. As an example, the trained classifier (or a collection of additionally trained classifiers) may be configured to determine different aspects of structural integrity of a wooden specimen. For instance, a classifier may be trained to determine a quality of one or more regions of the wooden specimen (and therefore a collective quality evaluation of the wooden specimen) based on analysis of the TOF data and the peak energy data, among other types of feature information. In further examples, a quality determination of a wooden specimen may be utilized to determine a remaining service life (e.g., remaining strength) of the wooden specimen based on a current quality of the wooden specimen and other impacting factors including but not limited to: environmental conditions of the wooden specimen, load conditions associated with the wooden specimen, insights and notes from visual inspection and physical dimensions of the wooden specimen, among other conditions that may affect longevity of a wooden specimen. An NDE report may further comprise an indication of the current quality of the wooden specimen, a net present value of the wooden specimen and/or the remaining service life.

Moreover, the computing device, executing an exemplary NDE application/service is configured to manage generated NDE reports. In some instances, an NDE report may be displayed on a computing device that the report is generated by and in other instances the NDE report may be generated by one computing device and transmitted to another for presentation. In some examples, an NDE report may be stored on a computing device in which the NDE report was generated. In other examples, an NDE report may be transmitted to another device or a distributed storage (e.g., cloud-based storage). For instance, the NDE application/service may be configured to generate an NDE report and transmit the NDE report to a database or email server of a user, among other non-limiting examples.

Additional non-limiting examples extend to a user interface experience that is specifically tailored to the management of NDE of a wooden specimen. In addition to extensibility providing utility that was not previously available, an NDE application/service is specifically programmed to improve a user experience when executing NDE of a wooden specimen. For instance, a user may launch an NDE application/service on a computing device. A GUI of an NDE application/service is specifically configured to enable management of data required for NDE of wooden specimen. The NDE application/service may provide user interface features and/or data fields enabling inspectors to customize a testing experience through data entry. The GUI enables users to enter customized testing parameters that may relate to a specific testing scenario. Examples of parameters that may be entered comprise but are not limited to: testing identification data (e.g., name, date, location, specimen identification tags, inspector identification, testing configurations such as a set number of testing points; physical characteristics of the wooden specimen (including physical dimensions); load conditions affecting the wooden specimen; environmental conditions associated with the wooden specimen; variables and rules for data modeling analysis; source files for collecting/accessing acoustic signal data for analytical evaluation; and other associated settings as described herein, among other examples.

Further non-limiting examples, reference interfacing between an exemplary computing device that is executing an NDE application/service and one or more NDE devices that are utilized for NDE of wooden specimen. An exemplary NDE device may comprise: a transducer assembly that comprises an acoustic transducer (e.g., an ultrasonic transducer); an electronic processing assembly that comprises a printed circuit assembly and a processing unit; and a casing assembly, that houses the transducer assembly and the electronic processing assembly. The casing assembly is configured, at an end portion, to attach to a testing object that is inserted into a wooden specimen such as a wooden cylinder or a wooden utility pole. The NDE device may be configured to receive, from the acoustic transducer, acoustic signal data and transmit, to a computing device, the acoustic signal data via a data transmission component of its processing unit. In additional examples described herein, multiple NDE devices may be attached to a wooden specimen, via multiple testing objects, to enable more comprehensive testing of structural integrity of a wooden specimen. For example, a first NDE device may be configured as a transmitting device, for transmitting of acoustic signal data, and a second NDE device may be configured as a receiving device to receive transmitted acoustic signal data. Data from both devices may be propagated to a computing device that may be configured to analyze the acoustic signal data. In further examples, an NDE application/service may be utilized to control NDE of a wooden specimen. For instance, control commands may be transmitted to check a connection between an NDE device and a waveguide or manage scientific parameters (e.g., voltage) propagated through an exemplary waveguide, among other examples.

Turning back to the NDE application/service, the GUI of the NDE application/service is further configured to enable users to execute processing operations for NDE of a wooden specimen. For example, user interface features may be provided through the GUI to initiate signal feasibility testing for evaluation as to whether a received signal is sufficient for proper NDE analysis to be performed; initiate signal data transmission for NDE of a wooden specimen; and NDE report generation. In some examples, the NDE application/service is automatically configured to generate an NDE report based upon completion of analysis of an acoustic signal (e.g., ultrasonic signal). In one instance, a user may select a user interface feature to initiate NDE of a wooden specimen such as after signal feasibility testing has been approved and testing parameters have been entered into the NDE application/service. This may be a trigger for the computing device to transmit one or more control commands to an NDE device (or multiple NDE devices) to initiate NDE of a wooden specimen. For instance, one or more NDE devices may be attached to a wooden specimen, where the NDE devices comprise a data transmission component that enables said NDE device to send/receive signals to/from a computing device. In response to conducting NDE of a wooden specimen, the one or more NDE devices may transmit collected acoustic signal data to the computing device for NDE analysis. As such, a computing device, executing the NDE application/service, may receive acoustic signal data from the one or more NDE devices and initiate NDE analysis.

As indicated in the foregoing description, an NDE report may comprise any data from NDE analysis described herein. Waveform analysis of the received acoustic signal data transmitted through and around regions of a wooden specimen may yield cross-sectional analyses of the wooden specimen. The NDE application/service may be configured to generate illustrative representations of the different cross-sectional analyses for presentation in an NDE report. For example, graphical representations of different cross-sectional analyses may be generated into three-dimensional views of the internal structure of a wooden specimen, which can then be presented through a GUI of an NDE application/service and/or in an NDE report for further inspection. This may provide reviewers with additional insights into the structural integrity of a wooden specimen.

Among other technical benefits, the present disclosure provides the following technical advantages over previous methods of testing structural integrity of a wooden specimen: introduction of an NDE application/service that is tailored to NDE of a wooden specimen; providing an improved GUI that correlates user interface features and data fields for NDE of a wooden specimen; ability to control operation of an NDE device and conduct NDE of a wooden specimen wirelessly, where testing data can efficiently synchronized with a testers' computing device and memorialized, via data storage such as distributed data storage, for further evaluation; ability to obtain raw acoustic waveforms and other data directly from a device that is attached to a wooden specimen; ability to extract features from acoustic waveforms, acoustic attenuation, spectrogram and composite TOF measurements that are derived from algorithms that are applied as described herein; generating and applying machine learning modeling for wooden specimen classification as well as forecasting projections about one or more wooden specimen; ability to compute quality of a wooden specimen (e.g., moduli/strength) based on extracted features; ability to mount an NDE device to a wooden specimen in a hands-free configuration; improved accuracy in evaluating structural integrity of a wooden specimen including wooden structures; ability to generate customized NDE reports as described herein; ability to generate visual representations (e.g., three-dimensional visualizations) of a structural integrity of a wooden specimen for subsequent analysis; improved processing efficiency (e.g., reduction in processing cycles, saving resources/bandwidth) for computing devices when executing NDE of a wooden specimen; reduction in latency during collection of acoustic signal data and provision of NDE results; and improving usability of applications/services for conducting NDE of wooden specimen, among other technical advantages.

FIG. 1 illustrates flow diagram 100 of analysis executed by a non-destructive evaluation (NDE) application/service for evaluating wooden specimen, with which aspects of the present disclosure may be practiced. Flow diagram 100 illustrates a high-level overview of an overall analysis of NDE of a wooden specimen as described in the present disclosure, where an NDE application/service is configured and programmed to execute operations for wooden specimen analysis and forecasting of conditions and projections of the wooden specimen (e.g., net present value of one or more wooden specimen, future condition of the wooden specimen and future value of the one or more wooden specimen). As identified in the foregoing description, the NDE application/service is configured to execute processing operations that are usable to programmatically classify a wooden specimen. This may occur without the need for an inspector to manually assess a condition of a wooden specimen, though the GUI may be configurable to enable inspector input/comments to be entered as testing parameters to improve the performance of classification processing described herein. The NDE application/service comprises source code that software configured to execute the processing operations described herein. An exemplary NDE application/service may be configured to execute algorithmic processing (including one or more specific algorithms) to achieve processing operations described herein. Means of executing the described processing operations through software implementation are known to one skilled in the field of art.

Execution of software associated with an NDE application/service comprises execution of trained data modeling that is specifically optimized to execute processing operations described herein. For instance, the NDE application/service is configured to implement one or more algorithms based on governing principles of wave propagation. Furthermore, the NDE application/service is configured to implement data modeling that employs a trained classifier to determine structural integrity of a wooden specimen (e.g., a condition and quality of a wooden specimen). Data modeling implemented may further be configured to evaluate other characteristics associated with a wooden specimen to execute predictive modeling that can assist network managers with making informed decisions for planning and budgeting around networks of wooden specimen. A classifier may be an artificial intelligence (AI) classifier that continuously evolves to improve classification processing. Non-limiting examples of an AI classifier comprise but are not limited to deep learning modeling such as machine learning processing and/or neural network processing. Processing operations for generating, training and implementing an AI classifier are known t one skilled in the field of art.

Process flow diagram 100 begins at processing operation 102, indicating a receipt of acoustic signal data (e.g., ultrasonic signal data) associated with a wooden specimen for analysis of the wooden specimen. For ease of explanation, a wooden specimen is a wooden utility pole, where analysis relates to the structural integrity of the wooden utility pole. Acoustic signal data may be received at a computing device, where the acoustic signal data related to NDE of the wooden utility pole (i.e., the ultrasonic signal data is transmitted through the wooden utility pole). An exemplary computing device is a computing device that is executing an NDE application/service. In one instance, a user may select a user interface feature to initiate NDE of a wooden specimen such as after signal feasibility testing requirements have been satisfied and testing parameters have been entered into the NDE application/service. This may be a trigger for the computing device to transmit one or more control commands to an NDE device (or multiple NDE devices) to initiate NDE of a wooden specimen. For instance, one or more NDE devices may be attached to a wooden specimen, where the NDE devices comprise a data transmission component that enables said NDE device to send/receive signals to/from a computing device. In response to conducting NDE of a wooden specimen, one or more NDE devices may transmit collected acoustic signal data to the computing device for NDE analysis. As such, a computing device, executing the NDE application/service, may receive (processing operation 102) acoustic signal data from the one or more NDE devices and initiate NDE analysis. Additionally, data transmission of acoustic signal data and resulting subsequent analysis further differentiates from what may be traditionally known by transmission of acoustic signals both through and around a surface of a wooden specimen in one or more regions of the wooden specimen. This enables more comprehensive analysis of a region of a wooden specimen, for example, where energy attenuation can be examined both through and around a region of the wooden specimen.

Flow of diagram 100 may proceed to processing operation 104, where analysis (e.g., pole strength analysis) of a wooden utility pole occurs. Processing operation 104 comprises processing operations such as: detecting waveforms in received acoustic signal data; extracting critical parameters and features associated with detected waveforms (including arrival regions of waveforms); applying trained data modeling to classifying a condition the structural integrity of a wooden specimen (e.g., condition and/or quality analysis of the wooden specimen); and applying trained data modeling to forecast an impact of a wooden specimen (present and/or future) on a network that comprises a plurality of wooden specimen (e.g., wooden utility poles). For instance, detection processing of waveforms in received acoustic data may comprise: identifying one or more arrival waveforms in a specific region of a wooden specimen that go through the wooden specimen; and identifying arrival waveforms in a specific region of a wooden specimen that go around a surface of a wooden specimen. This enables more comprehensive analysis of a region of a wooden specimen, for example, where energy attenuation can be examined both through and around a region of the wooden specimen, where a combined energy and TOF analysis provides trajectory attenuation, which enables inferences of quality (e.g., density and strength) of a wooden specimen. Scientific processing operations for arrival feature detection and evaluation of waveforms are known to one skilled in the field of art and are not described herein. Such features may be programmed into execution of an NDE application/service, specifically, data modeling that is used to analysis of signal data for an acoustic signal. Additionally, extraction of features from said detected arrival waveforms may comprise TOF and peak energy and/or frequency, among other scientific parameters, for evaluating a representative waveform that goes through a region of a wooden specimen and a representative waveform that goes around a region of a wooden specimen. Said features may be utilized to formulate a comprehensive analysis of energy attenuation levels in region of a wooden specimen as well as a wooden specimen as a whole.

As indicated in the foregoing description, analysis of a wooden specimen comprises one or more of: classification of a condition of the wooden specimen, classification of a quality of the wooden specimen and/or a strength analysis of the wooden specimen. Additionally, analysis of a wooden specimen may further comprise: forecasting of an impact of a wooden specimen (present and long-term,) for example, based on its present condition, external conditions affecting the wooden specimen and/or a position of the wooden specimen in a network of wooden specimen (e.g., population or grouping of wooden utility poles), among other examples. Non-limiting examples of metrics that may be generated for classification of a condition of a wooden specimen comprise but are not limited to: metrics related to classification of a condition of a wooden specimen; metrics related to material strength of a wooden specimen; metrics related to remaining material strength of a wooden specimen; net present value of a wooden specimen; life expectancy/replacement estimations (present and/or future) for a wooden specimen; and projected net value of the wooden specimen at a future point in time based on the present condition of the wooden specimen, among other examples.

Results of analysis of a wooden specimen (e.g., pole inspection analysis of a wooden utility pole) may be stored for data logging at processing operation 106. For example, a pole inspection analysis result may be generated for analysis of a wooden utility pole. The pole inspection analysis result may be stored in a data storage for future reference in subsequent inspections of that wooden specimen or similar types of wooden specimen. Non-limiting examples of a data storage comprise but are not limited to: local data storage for the computing device, external data storage connected with the computing device, and distributed network storage accessed via a network connection, among other examples. In one example, the data storage may be a distributed data storage that is accessible, via a network connection, to the data modeling of the NDE application/service during analysis of a wooden specimen.

Results of analysis of a wooden specimen may further be propagated for subsequent analysis such as network health analysis of a wooden specimen (processing operation 108). As described in the foregoing description, network health analysis may comprise assessment of a plurality of wooden specimen, where the wooden specimen may be grouped with other wooden specimen to generate an overall assessment of a network or population of wooden specimen (e.g., sample population of wooden utility poles). Processing operation 108 may comprise operations related to identification of other similar/related wooden specimen (e.g., type of wooden specimen, location, owned or managed by a specific organization) and retrieval of wooden specimen analysis results associated with similar/related wooden specimen. For example, data modeling executes a trained classifier, based on historical data of similarly grouped wooden specimen, to analyze results for a grouping of wooden utility poles at a specific location. Data for similarly grouped wooden specimen may be collected, aggregated and used to evaluate the network of wooden specimen, thereby providing a subset of data that can be further analyzed to identify metrics for an overall condition of that network of wooden specimen, determine the net present value of the network of wooden specimen and forecast future condition and/or value of the network of wooden specimen.

A database of inspection analysis results may be maintained for an NDE application/service to access, parse and cross-reference. Process flow 100 illustrates an exemplary database labeled as a network condition database. Data modeling may be applied to analyze said data and generate network health analysis metrics assessing present and/or future projections associated with wooden specimen. Furthermore, in additional examples, the NDE application/service may further be configured to access and cross-reference a library of sample waveform data (e.g., arrival waveform data) that corresponds to specific types of wooden specimen. For instance, the library of sample waveform data may be a web resource (e.g., database of wood specimen managed by an entity such as a business, organization, university) that is accessible via network connection. Said library data can be further utilized to aid projections for wooden specimen, especially in early stages of network analysis where a large corpus of data has not yet been established. While the library of sample waveform data may not necessarily reflect data that is obtained via NDE evaluation, an eventual goal is to obtain a corpus of data from past NDE that can be utilized to help improve wooden specimen analysis and network health analysis. A database of inspection analysis results may also serve as a quality control platform to evaluate the inspection quality and to improve performance of a trained classifier.

Data for a network of wooden specimen may be propagated to data modeling for a network healthy analysis evaluation. Flow of diagram 100 may process to processing operation 110, where data modeling is applied to execute a network health analysis for a network of wooden specimen. As identified in the foregoing description, data modeling may employ a trained classifier to generate network health analysis metrics for a network of wooden specimen. A network health segment may explore hidden features within a database of inspection analysis results using trained data modeling (e.g., machine learning processing) to evaluate and forecast health conditions of one or more wooden specimen. Non-limiting examples of network health analysis metrics that may be generated to evaluate and forecast health conditions of a network of wooden specimen comprise but are not limited to: metrics related to classification of condition and/or structural integrity of a network of wooden specimen; net present value of a network of wooden specimen based on present condition of the network of wooden specimen; life expectancy/replacement estimations (present and/or future) for a network of wooden specimen based on the present condition of the network of wooden specimen; and projected net value of the network of wooden specimen at a future point in time based on the present condition of the network of wooden specimen, among other examples. Similar to inspection results for a single wooden specimen, inspection results for a network of wooden specimen (pertaining to network health analysis) may also be stored on an exemplary data storage for access including generation of an NDE report.

At processing operation 112, an NDE report is generated. An exemplary NDE report may be a network health report that represents a state of a wooden specimen, a network of wooden specimen or a combination thereof. An NDE report may comprise any of the above identified features resulting from execution of data modeling utilizing the trained classifier as well as any other data that would further (or add context to) NDE of a wooden specimen including entered testing parameters and notations (e.g., from an inspector), among other examples. A format of an NDE be any type of electronic document as known to one skilled in the field of art. Non-limiting examples of an NDE report comprise but are not limited to: a portable document format (PDF); data objects (e.g., JavaScript Object Notation (JSON) objects); web documents (e.g., a web page); electronic documents generated in formats compatible with cloud-based software services, and quality assurance report documents, among other examples.

In one example, an NDE report (network health report) may be programmatically generated based on results of data modeling processing. For instance, the trained classifier is further configured to aggregate analyzed results for inclusion in an NDE report and generate the NDE report for presentation. In other examples, processing for generation and surfacing of an NDE report may be the result of programmed software instructions written into the code of the NDE application/service rather than requiring data modeling to generate the NDE report. In some other examples, generation of an NDE report may be the result of a user interface selection within a GUI of an NDE application/service. For instance, a GUI of the NDE application/service may notify a user that analysis of a wooden specimen is complete and give the user the opportunity to select when to generate the NDE report.

As previously referenced, an NDE report may be customized based on parameters entered by a user through a GUI of an NDE application/service. For example, a GUI may be configured to provide GUI elements enabling a user to select a format for an NDE report as well as specific types of data that a user wishes to include in an NDE report. As such, an NDE report can be contextually tailored as per user requests. In other examples, an NDE report may be generated on behalf of a user without a user being given the opportunity to toggle aspects of an NDE report. A generated NDE report may be presented through one or more of: a GUI of an NDE application/service and an application/service that is associated with a selected format of the NDE report as identified in the GUI of the NDE application/service.

As indicated in the foregoing description, an NDE report may comprise any data from NDE analysis described herein. Waveform analysis of the received acoustic signal data transmitted through and around regions of a wooden specimen may yield cross-sectional analyses of the wooden specimen. The NDE application/service may be configured to generate illustrative representations (visualizations) of the different cross-sectional analyses for presentation in an NDE report. For example, graphical representations of different cross-sectional analyses may be generated into three-dimensional views of the internal structure of a wooden specimen, which can then be presented through a GUI of an NDE application/service and/or in an NDE report for further inspection. This may provide reviewers with additional insights into the structural integrity of a wooden specimen.

Figure 2:
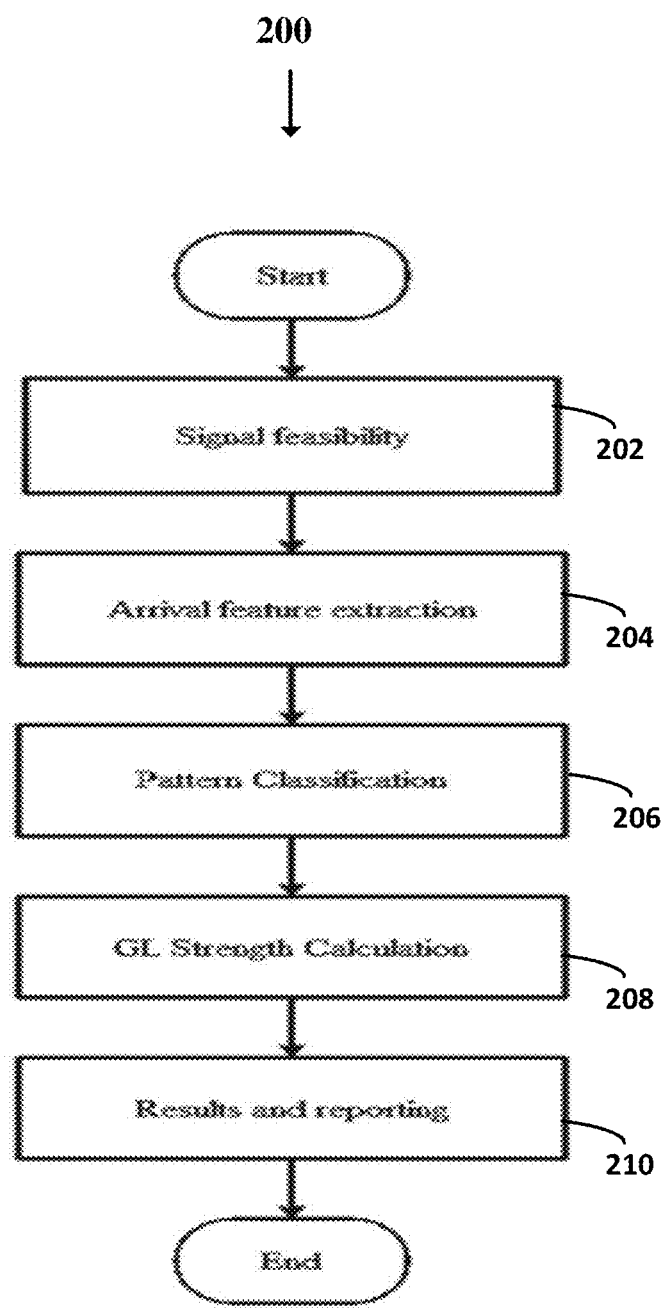
FIG. 2 illustrates a flow diagram highlighting specific processing operations executed during NDE of a wooden specimen, with which aspects of the present disclosure may be practiced.

FIG. 2 illustrates a flow diagram 200 highlighting specific processing operations executed during NDE of a wooden specimen, with which aspects of the present disclosure may be practiced. Flow diagram 200 illustrates a high-level overview of processing operations that are executed during NDE processing. NDE processing, as described herein, comprises five routines: signal feasibility processing 202; arrival feature extraction processing 204; pattern classification processing 206; specimen strength calculation processing 208, and results/reporting processing 210. While flow diagram 200 illustrates an exemplary order of execution of said NDE processing operations, each individual processing operation provided in flow diagram 200 is explained in further detail in subsequent figures (e.g., description of FIGS. 3-5, and 7-8). It is to be further understood that NDE processing operations illustrated in flow diagram 200 may be executed in a different order from that shown in flow diagram 200 without departing from the spirit of the present disclosure.

Figure 3:
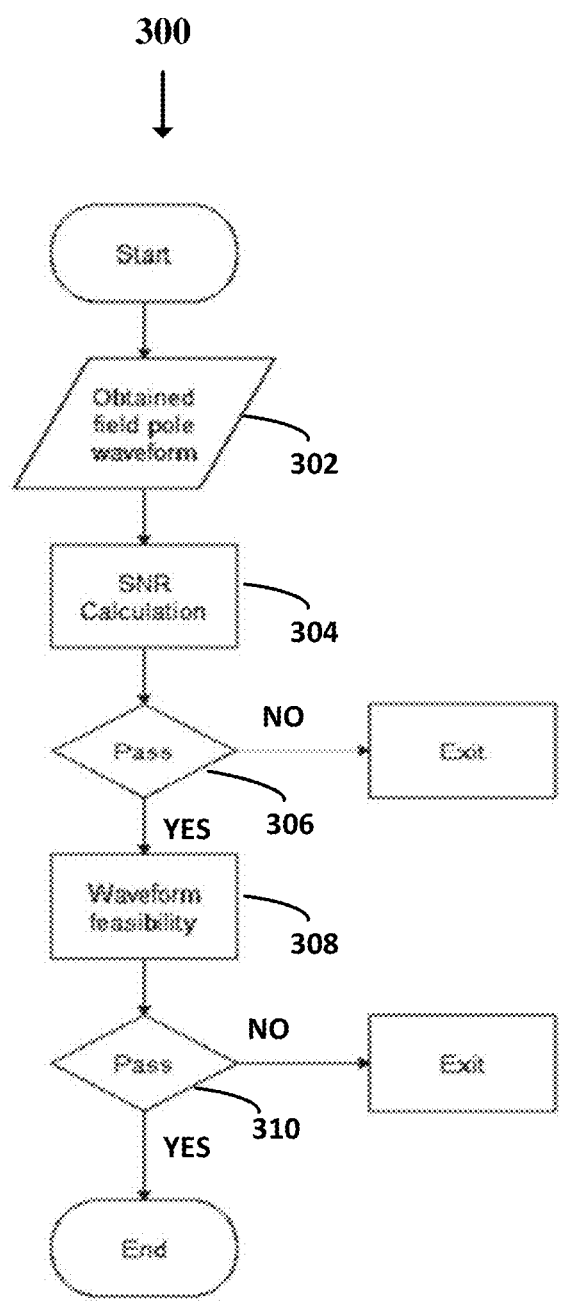
FIG. 3 illustrates a flow diagram highlighting signal feasibility analysis for NDE evaluation of a wooden specimen, with which aspects of the present disclosure may be practiced.

FIG. 3 illustrates a flow diagram 300 highlighting signal feasibility analysis for NDE evaluation of a wooden specimen, with which aspects of the present disclosure may be practiced. Signal feasibility analysis (e.g., signal feasibility processing 202 of FIG. 2) determines whether a received signal satisfies a set of predefined requirements for the subsequent analyses. In one example, the signal feasibility analysis is a testing phase that confirms that a computing device executing an NDE application/service is properly interfacing with one or more NDE devices to conduct proper NDE of a wooden specimen. For instance, a connection of an NDE device with a testing object (that is attached to a wooden specimen) may be poorly made resulting in a weak acoustic signal that is insufficient for accurately executing NDE of a wooden specimen. Before NDE commences, signal feasibility testing is performed. This improves efficiency of NDE processing as to avoid executing NDE analysis on a signal that would not be able to generate useful results. Predefined requirements for signal feasibility testing may be set by developers and vary without departing from the spirit of the present disclosure. In one example, predefined requirements are predefined based on prior field testing results for NDE of wooden specimen. In further examples, predefined thresholds for signal feasibility testing may correspond with a predetermined optimal resonance frequency of a material used to fabricate an NDE device, a component thereof (e.g., ultrasonic transducer) and/or testing objects used to transmit an acoustic signal.

Flow diagram 300 initiates at processing operation 302, where acoustic signal data (e.g., ultrasonic signal data) is obtained. In one example, the acoustic signal data obtained is a testing signal that is used to validate that a device has been properly connected to a wooden specimen before NDE processing commences. In another example, the acoustic signal data is the actual signal that NDE processing will commence on. In the latter case, an error message would appear in the GUI if the signal does not satisfy signal feasibility requirements, requiring re-initiation of NDE processing. As an example, the computing device executing the NDE application/service may be configured to transmit a command to an NDE device to propagate an ultrasonic signal (e.g., testing signal or otherwise) through a wooden specimen. The NDE application/service is configured to verify that the predefined requirements are satisfied for actual NDE to commence. In some technical instances, the NDE application/service may be configured so that a user may select a GUI feature of the NDE application/service to initiate signal feasibility testing. In other examples, an NDE application/service is configured to automatically detect connection of an NDE device with an NDE application/service, which acts as a trigger to automate signal feasibility analysis without requiring user input. In further examples, a GUI of an NDE application/service may help guide a user with confirming that signal feasibility testing requirements are satisfied. For instance, if a portion of signal feasibility analysis has failed, a notification may be automatically provided to a user through a GUI of the NDE application/service. An acoustic signal may be transmitted through a wooden specimen and returned to an NDE device, which transmits, via a data transmission component, the signal to a computing device executing the NDE application/service for signal feasibility analysis. An obtained signal (e.g., ultrasonic signal waveform) is analyzed at the computing device.

Signal feasibility analysis measures signal data using the following two criteria. The first one is the signal-to-noise ratio (SNR), which is a metric to calculate the signal strength compared to the noise level that is intrinsic to any electronics. Processing operation 304 illustrates executing of SNR calculation to evaluate the strength of an obtained signal data. If the signal strength is too low, the later routines will not be able to resolve the proper TOF and the energy attenuation. Hence, signal feasibility processing compares the calculated SNR to the minimal SNR threshold.

Flow of flow diagram 300 may proceed to decision operation 306, where it is determined whether obtained signal data satisfies a minimal SNR threshold. If a minimal SNR threshold is not satisfied, signal feasibility testing fails leading to the end of signal feasibility analysis. As referenced in the foregoing description, this may result in an update of a GUI of the NDE application/service to notify the user that signal feasibility requirements have not been satisfied. In examples where a SNR threshold is satisfied, flow of signal feasibility analysis continues to processing operation 308, where a second criterion, waveform feasibility, is evaluated.

Processing operation 308 evaluates the feasibility of a waveform of obtained signal data. The obtained waveform must contain essential characteristics based on the physical model and the prior knowledge. In a case when external interference, false mounting technique or electronic errors occurs, the waveform signal is deemed unfit for subsequent analyses. This may be informed by a waveform not reflecting proper characteristics for NDE analysis. If it is determined that a waveform does not reflect proper waveform characteristics for NDE analysis, signal feasibility testing fails leading to the end of signal feasibility analysis. As referenced in the foregoing description, this may result in an update of a GUI of the NDE application/service to notify the user that signal feasibility requirements have not been satisfied. In examples where it is determined that a waveform does reflect proper waveform characteristics for NDE analysis, flow of signal feasibility analysis continues to processing operation 310, where it is identified that waveform feasibility evaluation has passed. When all criteria are met, the signal is sent to the next level of analysis. Even if a threshold is not satisfied, exit of software program may still result in the resulting waveform being provided to a user (i.e. inspector) for separate evaluation. This may assist with troubleshooting.

Figure 4:
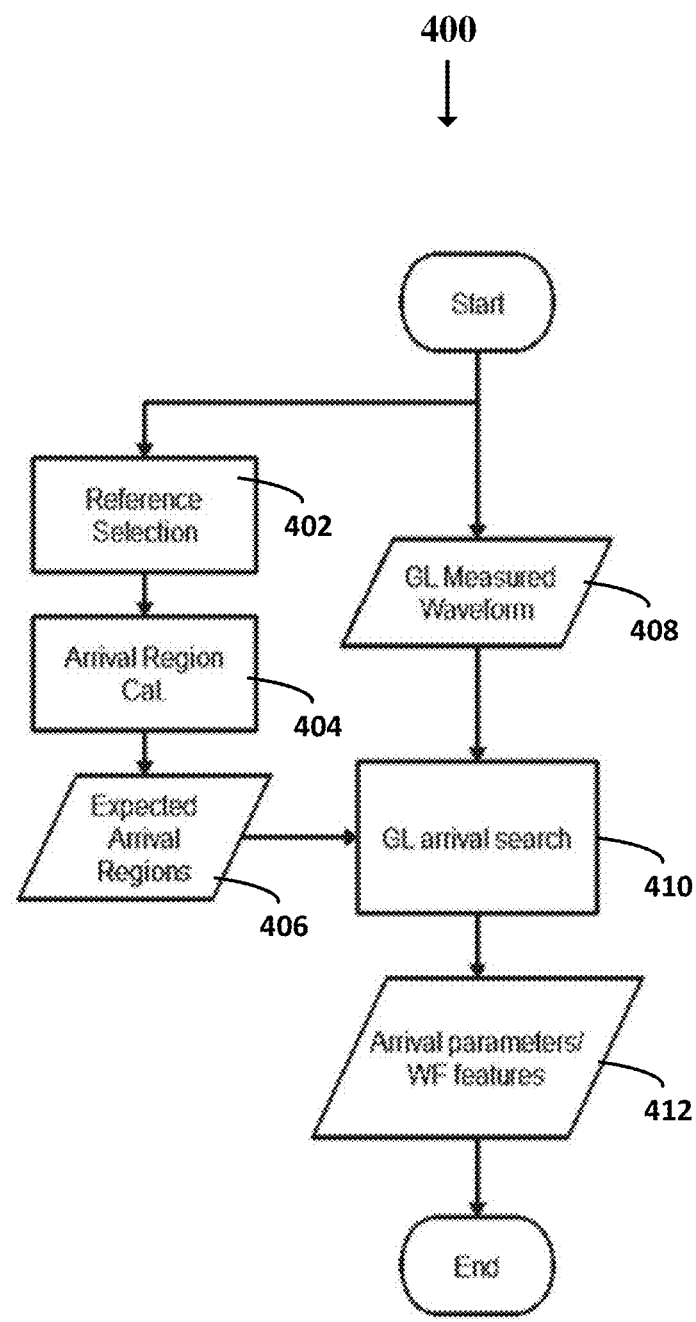
FIG. 4 illustrates a flow diagram highlighting feature extraction for NDE evaluation of a wooden specimen, with which aspects of the present disclosure may be practiced.

FIG. 4 illustrates a flow diagram 400 highlighting feature extraction for NDE evaluation of a wooden specimen, with which aspects of the present disclosure may be practiced. Arrival feature extraction (e.g., arrival feature extraction processing 204 of FIG. 2) extracts relevant features associated with the mechanical conditions hidden in the measured waveform. The feature classification routine uses the extracted features and a trained classifier to determine the mechanical condition of a wooden specimen. In an example where a wooden specimen is a wooden utility pole, acoustic signal data may be obtained at a ground line (GL) of the wooden utility pole and/or other regions above the GL of the wooden utility pole. To provide most efficient analysis, a reference threshold should be taken for testing. At processing operation 402, a reference selection is made. A reference threshold may be a reference point to compare with real-time (or near real-time) signal data. In one example, a reference threshold may be a GL of a healthy wooden specimen (e.g., healthy wooden utility pole) of the same type and dimensions. However, any type of threshold data can be selected as a reference source. Feature extraction may occur on a reference threshold as well as additional regions of a wooden specimen that are being tested to enable comparative analysis to best classify a condition of a wooden specimen.

A region of a wooden specimen (e.g., wooden utility pole) that is being tested, and is not a reference threshold, may be classified as a manual threshold (or field threshold). For instance, a manual threshold may be one or more points of a wooden specimen such as points above a GL to compare with a GL threshold and/or a reference threshold. Having multiple analysis points on a wooden pole may enable more accurate analysis of the wooden specimen to determine and forecast future decay of the wooden specimen (e.g., for network health analysis). However, it is to be understood that NDE analysis can be executed using a single point of reference for NDE of a wooden specimen without departing from the spirit of the present disclosure.

In one example, one manual threshold (or field threshold) is the GL of a wooden utility pole. This is because incipient decay often starts right above the GL (e.g., six inches above grade), making that an optimal place to test the structural integrity of a wooden utility pole. It is to be understood that testing may occur at any portion of the wooden utility pole without departing from the spirit of the present disclosure. Inspectors may select optimal placement positions NDE devices based on any number of factors including but not limited to: different environmental conditions; analysis of NDE testing data (e.g., indicating patterns in testing data that may indicate most accurate testing results); and visual inspection of a wooden utility pole, among other examples. In some examples, baseline readings may be obtained at the GL or proximate to the GL (e.g., six inches above), where additional rounds of testing may adjust placement of NDE devices to compare with the baseline readings.

In some examples, a reference threshold may be library data obtained from another resource (e.g., web resource, database of wooden specimen data). For instance, a database may be maintained comprising data of a variety of wooden utility poles of different physical dimensions, wood types, locations, etc. Such data may be used to compare with analysis results from real-time (or near real-time) NDE processing on one or more wooden specimen. As referenced above, a reference threshold may be a healthy wooden pole of the same wood type as the wooden specimen that is being evaluated. In some alternative instances, a manual (or field) threshold may be utilized as a reference source for testing of a wooden utility pole. Traditionally, using a manual threshold as a reference source could cause less reliable results for detection because the signal characteristics can change gradually with a change in pole circumferences that may correlate with different portions of a wooden pole. The present disclosure accounts such cases by training a classifier to take into consideration this gradual change in variation circumference of a wooden specimen when a manual threshold is utilized as a reference source for classifying one or more regions of a wooden specimen. Traditionally, a circumference of a wooden utility pole reduces as the measurement is taken higher and higher from the GL. Hence, the change in this dimension causes a change in a signal as it propagates through/around a wooden utility pole. A classifier is trained to account for this, where a testing point (manual threshold/field threshold) that is above the GL results in an adjusted waveform thereby generating a more accurate comparative analysis of regions of a wooden specimen.

Once a proper reference threshold is identified, a source file identifying the reference threshold is identified for analysis using said data modeling. The source file may contain sample waveform data for the reference threshold (e.g., a wooden utility pole of the same type, dimensions, etc.). Processing operations 404-406 correspond to analysis of said sample waveform data to calculate points of reference in time so that specific waveform features can be extracted for analysis. The characteristics of arrival waves of ultrasonic signal data in the measured waveform correlate to various conditions in various regions of the wooden specimen. For example, if two NDE devices/probes are positioned at a cross-sectional plane of a wooden utility pole, the first arrival waveform corresponds to an acoustic wave propagating radially, and the second arrival waveform corresponds to a waveform propagating tangentially around a cross-sectional region of the wooden utility pole. The feature extraction processing extracts (processing operation 404) the arrival characteristics embedded in the waveform signal for the reference sample. Flow of flow diagram 400 may proceed to processing operation 406, where expected arrival regions are determined for the reference sample. In one example, an inspector selects a reference threshold from a library set of healthy wood poles with the same dimensions to calculate the expected arrival regions (processing operation 406) for identifying features from specific waveforms. Within each arrival region, an employed search subroutine detects the arrivals within each expected arrival region for a region of the wooden specimen being evaluated (e.g., reference sample and subsequently the ultrasonic waveform that is being evaluated during NDE). The exact occurrence in time of the energy peaks and the energy values are stored to become arrival features for the pattern classification processing. This data can be propagated to assist with identifying arrival features of an ultrasonic waveform that that is being evaluated in real-time (or near real-time) (processing operation 410).

Processing operations 408-412 correspond with evaluation of a ground line threshold (or field threshold) that NDE is being performed on. As referenced above, an exemplary manual threshold may be at a GL or proximate thereto (e.g., six inches above the ground line). At processing operation 408, a waveform is measured from the ultrasonic signal data. The measured waveform is searched (processing operation 410) to identify arrival characteristics based on the arrival regions obtained from a source reference. Measured waveform features from the arrival regions are then extracted (processing operation 412) for subsequent analyses, where data modeling may evaluate the TOF and/or peak energy of extracted features for a measured waveform and execute pattern classification analysis for said measured waveform.

Figure 5:
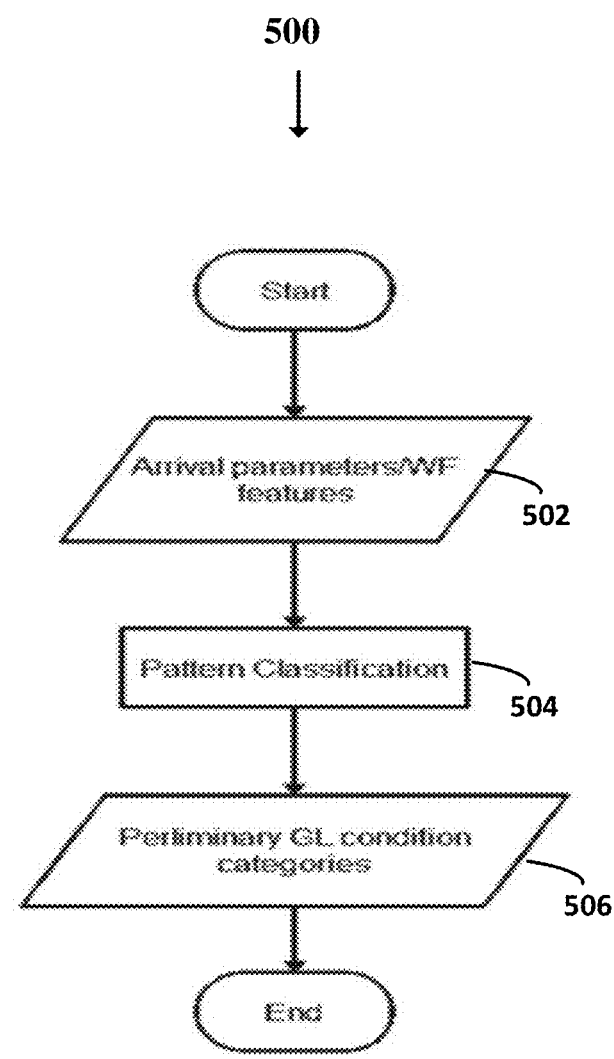
FIG. 5 illustrates a flow diagram highlighting pattern classification analysis for NDE evaluation of a wooden specimen, with which aspects of the present disclosure may be practiced.

FIG. 5 illustrates a flow diagram 500 highlighting pattern classification analysis for NDE evaluation of a wooden specimen, with which aspects of the present disclosure may be practiced. Pattern classification analysis (e.g., pattern classification processing 206 of FIG. 2) is processing that is usable to classify the structural integrity of a wooden specimen. The classifier is trained contains and developed using supervised or unsupervised learning techniques. In the case of supervised learning, the classifier is implemented through data modeling processing (e.g., machine learning processing) as described in the foregoing description. In doing so, the pattern classification analysis executes a subroutine that uses the arrival features generated from the feature extraction analysis to determine the condition of the wooden specimen. Using the training samples collected with the accurate labeling as to the classification of a wooden specimen, the classifier is constantly adjusted to minimize the mis-classification error and improve classification accuracy. For instance, training samples for pattern classification may comprise sample waveform data of a variety of different conditions of sample wooden specimen including but not limited to: healthy wooden specimen; unhealthy wooden specimen and any state therebetween. Training samples may be retrieved from any type of data source. Waveform data may be associated with such training samples, where waveform data that aligns with extracted features of ultrasonic signal data for NDE processing may be compared with sample waveform data of the training samples to best classify a condition of a wooden specimen. A linear or nonlinear classifier may be utilized to divide regions of a wooden specimen based on extracted feature values. Training of a classifier minimizes the mis-classification error in a non-separable case or eliminates mis-classification in a separable case. In particular, pattern classification may evaluate, compare and match attributes such as TOF and peak energy of waveform data in a signal that is being evaluated with that of the training samples. A classification is inferred from results of the comparison. For instance, classification levels may be set to indicate whether the NDE processing identifies whether the condition of the wooden specimen is good/healthy; in need of further monitoring/retesting at a specific point in time; or unhealthy/in need of immediate attention (e.g., replacement). Determined classification labels may correspond with a color-coded output (e.g., green, yellow red, respectively) that may be provided in an NDE report and/or GUI of an NDE application/service to provide visual cue to an inspector as to a condition of a wooden specimen. It is to be understood that developers can set and manage classification labels (including visual indicators for notification) in any manner without departing from the spirit of the present disclosure. A trained classifier may execute ranking processing, to best determine how extracted features of a wooden specimen match reference data. Execution of ranking processing for a trained classifier is known to one skilled in the field of art and is not specifically described herein.

Figure 6:
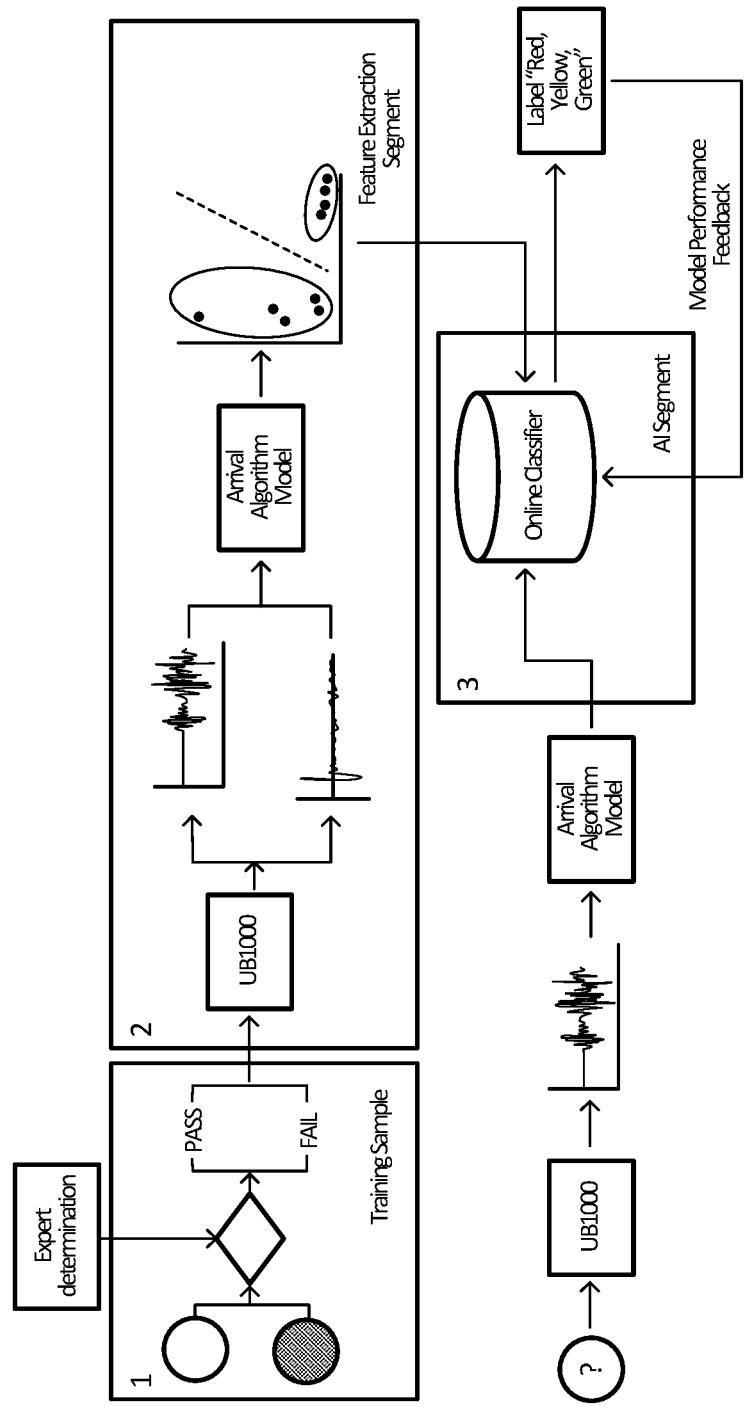
FIG. 6 illustrates a flow diagram for a system usable to conduct NDE of a wooden specimen, with which aspects of the present disclosure may be practiced.

FIG. 6 illustrates a flow diagram 600 for a system usable to conduct NDE of a wooden specimen, with which aspects of the present disclosure may be practiced. Flow diagram 600 illustrates a non-limiting example of training of an exemplary classifier, where processing steps labeled 1-3 in flow diagram 600 identify processing for training an AI classifier that is used to analysis signal data for NDE of a wooden specimen.

Process flow step 1 of flow diagram 600 comprises a visual inspection determination by an inspector field/expert. An inspector/field expert may first examine a wooden specimen (e.g., wooden utility pole) and identify various characteristics associated with the wooden specimen. In one example, process flow step 1 comprises a visual determination as to whether the wooden specimen passes or fails based on visual identification of whether the wooden specimen is healthy or decaying. However, it is to be understood that this determination may comprise collection of any of a plurality of characteristics associated with the wooden specimen, for example a use of drill to determine the interior condition, that can be utilized to improve classification analysis and projections and NDE reporting. Examples of associated characteristics that may be identified may factor into an analysis of a wooden specimen comprise but are not limited to: physical dimensions of the wooden specimen; environmental conditions affecting the wooden specimen; load conditions for the wooden specimen; a visual inspection state of the wood specimen (e.g., is it damaged, is there shell rot or some other form of visual decay); and notes or comments from an inspector (including other forms of testing/inspection performed or previously performed), among other examples. An inspector may assign a visual classification category of either pass or fail to the wooden specimen.

Flow diagram 600 may proceed to process flow step 2. At process flow step 2, the obtained features from the feature extraction processing are placed into a feature plot with other historical data of wooden specimen with similar attributes (e.g., dimensions, species, climate seasons). This data may be used for analyzing extracted features from received acoustic signal data, where processing from process flow step 2 is propagated to an exemplary classifier (e.g., online classifier).

At process flow step 3, of flow diagram 600, a classifier management subroutine updates the classifier position based on different objective functions, for example, minimizing the mis-classification error, or minimizing the squared-error of data samples. After the classifier is sufficiently trained, the resulted online classifier is used to help assign category for a pole with unknown condition. Flow diagram 600 further illustrates interactions where a trained classifier may be utilized to evaluate acoustic signal data received for NDE of a wooden specimen in real-time (or near real-time). For instance, an NDE device (e.g., labeled UB1000 in flow diagram 600) may receive acoustic signal data for NDE of a wooden specimen. Pertinent testing features may then be extracted as referenced in the description of at least FIG. 4, and the trained AI classifier may be applied to evaluate the extracted features. The AI classifier may execute a classification determination for a condition of the wooden specimen as described in at least the description of FIG. 5.

Figure 7:
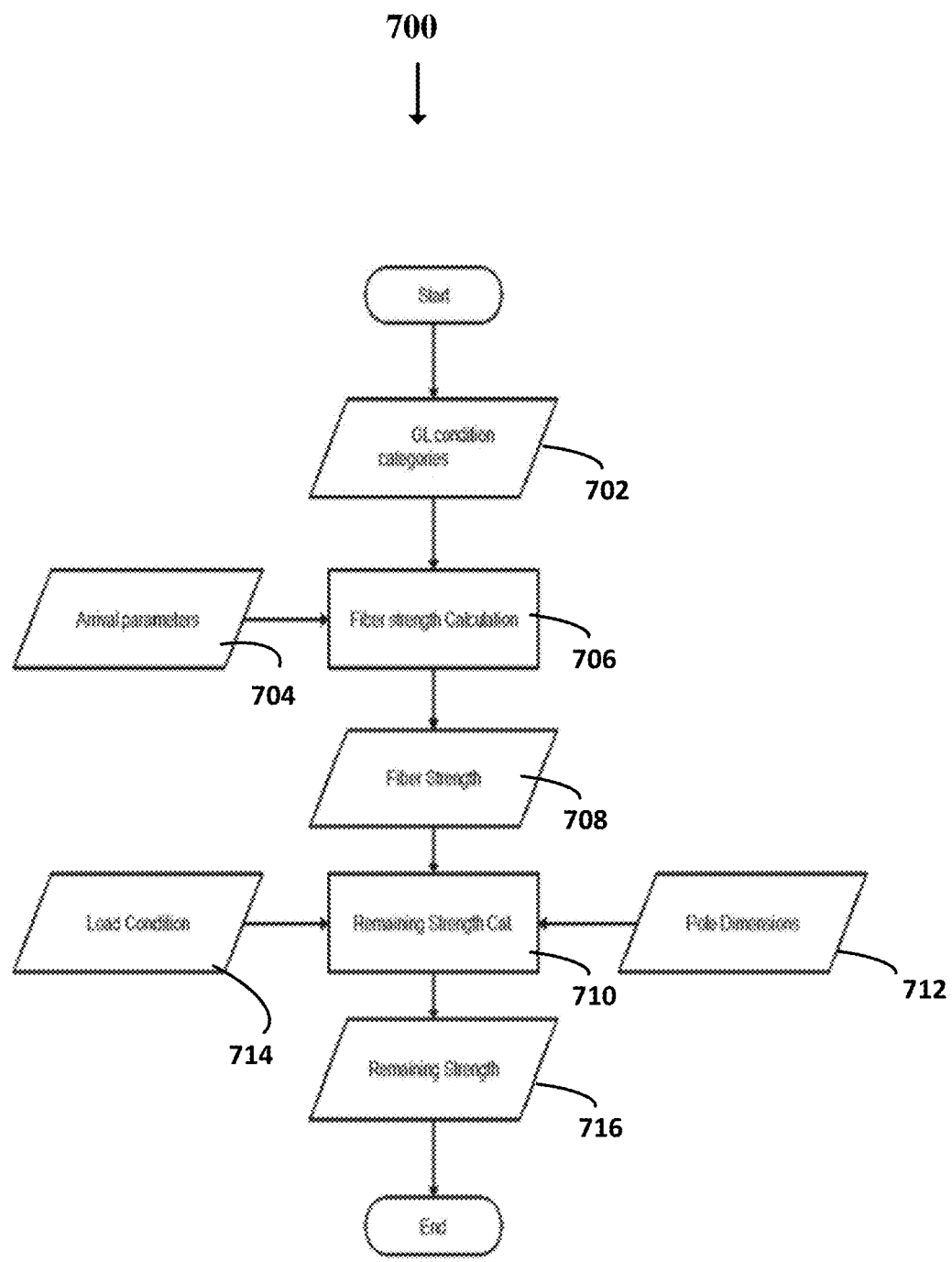
FIG. 7 illustrates a flow diagram highlighting strength calculation for NDE evaluation of a wooden specimen, with which aspects of the present disclosure may be practiced.

FIG. 7 illustrates a flow diagram 700 highlighting strength calculation for NDE evaluation of a wooden specimen, with which aspects of the present disclosure may be practiced. As referenced in the foregoing description, strength analysis may be a metric related to a quality determination of the wooden specimen, where quality evaluation may be executed in addition to a classification of a condition of a wooden specimen or to enhance classification of a condition of a wooden specimen. A combined energy and TOF analysis provides trajectory attenuation, which can infer density and strength of a wooden specimen. For instance, execution of a programmed NDE application/service employs a trained artificial intelligence (AI) classifier that evaluates waveform propagation (e.g., TOF and energy attenuation, frequency or other examples of known scientific parameters) through a wooden specimen to classify condition and remaining strength (e.g., remaining material strength) of the wooden specimen. For example, a remaining strength of the wooden specimen (in one or more regions and/or as a whole) may be determined and utilized to classify the structural integrity of the wooden specimen as well as forecast future projections for the wooden specimen. As an example, the trained classifier (or an additional trained classifier) may be configured to determine a material strength (e.g., fiber strength) of the one or more regions of the wooden specimen based on analysis of the TOF data and the peak energy data. In further examples, strength determination of a wooden specimen may project the remaining strength of the wooden specimen. The trained classifier is further trained to determine the remaining strength based on an analysis of: environmental conditions of the wooden specimen, load conditions associated with the wooden specimen and physical dimensions of the wooden specimen, among other conditions that may affect longevity of a wooden specimen. An NDE report may further comprises an indication of the material strength as its own metric and/or be utilized in the overall classification of the condition of the wooden specimen.

At processing operation 702, classification categorization is inferred from a pattern classification processing described in the foregoing description. This may comprise a classification of a wooden specimen at a manual threshold (field threshold) such as a GL of a wooden utility pole, where data modeling may utilize specific characteristics (e.g., energy intensity and/or attenuation) from a waveform analysis to assist in generating a strength estimation as to the strength of a wooden specimen. At processing operation 704, data modeling for may further access the arrival parameters of a measured waveform to obtain data necessary for material strength calculation.

Flow of flow diagram 700 may proceed to processing operation 706, where a strength of a wooden specimen calculation is generated. Using the inferred category and the arrival parameters of the measured waveform, a material strength calculation subroutine employs data modeling (e.g., a data-driven model and/or a physics model) to calculate the material strength by obtaining one or more of the modulus of rupture (MOR) and/or a modulus of elasticity (MOE) at the GL region. Scientific evaluation for calculating an MOR and/or MOE are known to one skilled in the field of art. In addition to numerically determining a material strength of a wooden specimen, the MOR and/or MOE metrics may further be utilized to determine a remaining material strength of the wooden specimen using projection data modeling based on historical, empirical data and simulated data. For example, based on present conditions of the wooden specimen at the GL threshold, manual threshold (or multiple points of the wooden specimen that NDE is performed) or combination thereof, a projection may be determined as to the remaining quality (e.g., remaining strength) of the wooden specimen. The remaining strength may be determined based on a result of said processing and subsequently propagated (processing operation 708) and may be included in NDE reporting.

Flow of flow diagram 700 may proceed to calculating the remaining strength of the wooden specimen (e.g., processing operation 710). The remaining strength may be determined from data modeling based on the calculated material strength as well as evaluation of physical dimensions of the wooden specimen (obtained in processing operation 712) and existing loading conditions and/or environmental conditions (obtained in processing operation 714). The remaining material strength may be output (processing operation 716) to be included in NDE reporting as well as forecast estimations and projections for the wooden specimen (e.g., net present value; replacement timeline; future value; inclusion in an evaluation of a network of wooden specimen).

Figure 8:
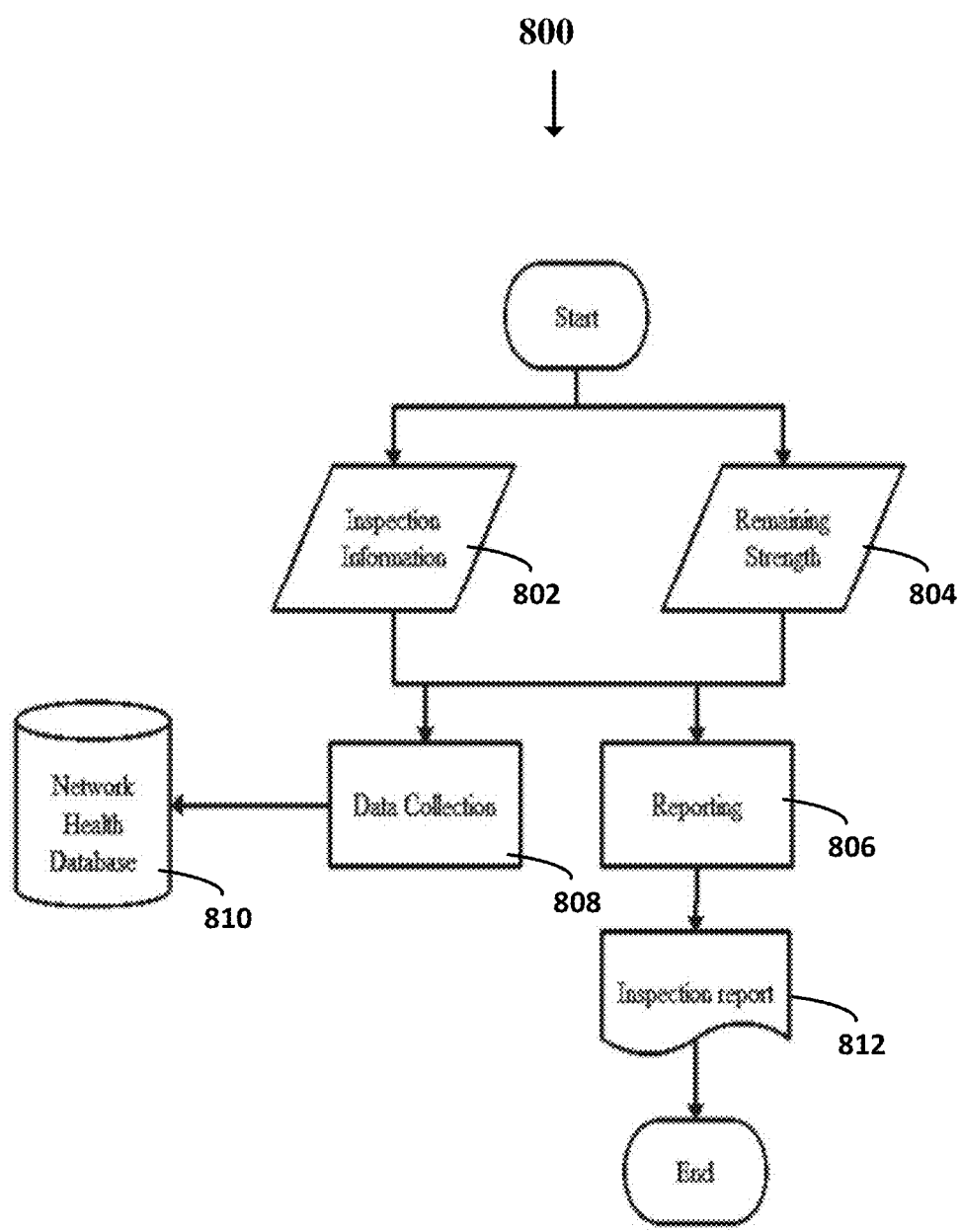
FIG. 8 illustrates a flow diagram highlighting data collection and reporting for NDE evaluation of a wooden specimen, with which aspects of the present disclosure may be practiced.

FIG. 8 illustrates a flow diagram 800 highlighting data collection and reporting for NDE evaluation of a wooden specimen, with which aspects of the present disclosure may be practiced. Data collection and reporting processing (results and reporting processing 210 of FIG. 2) may comprise processing operations to generate and present an NDE report providing results of NDE of a wooden specimen. Processing for generation of an NDE report as well as features included therein have been described in the foregoing description. Process flow diagram 800 highlights general processing for managing data associated with NDE of a wooden specimen to aid subsequent analysis as well as provide a detailed reporting of the NDE to users, for example, through a GUI of an NDE application/service. In other words, the goal of results and reporting processing is to populate wooden specimen analysis databases (e.g., network health database) to aid future analysis as well as provide inspection reports for wooden specimen assessments that detail NDE of one or more wooden specimen (e.g., one or more wooden utility poles).

Flow diagram 800 begins at processing operation 802, where inspection information is collected. Inspection information may pertain to data of an NDE that is entered through an NDE application/service (e.g., by a user such as an inspector) as well as results of NDE analysis of one or more regions of a wooden specimen, which may be collected for storage and inclusion in NDE reporting. Some non-limiting examples of inspection information may comprise information that is useful for comprehensive report generation including but not limited to: the inspection date; a location of the inspection; environmental conditions during testing; details about the wooden specimen and the NDE processing; inspector identification information; and information about NDE devices utilized, among other examples. Additionally, results of NDE analysis of quality metrics for the wooden specimen may further be collected (processing operation 804) for storage and inclusion in NDE reporting.

In some examples of processing of flow diagram 800, the collected data associated with the strength of the wooden specimen as well as the inspection information may be propagated to a data collection subroutine (processing operation 808) that results in the data being archived (processing operation 810) in a wooden specimen analysis database and/or network health database. This data may be leveraged to aid subsequent analysis, among other possible uses to provide a more comprehensive analysis of structural integrity of a wooden specimen.

A reporting subroutine (processing operation 806) may be executed to generate an inspection report about the assessment activity according to user specifications. As identified in the foregoing description, a GUI of an NDE application/service may be configured to enable users to customize NDE reporting through selection of relevant analytical features for presentation in an NDE report. At processing operation 806, the reporting subroutine is configured to identify parameters for NDE reporting, via the NDE application/service, and generate (processing operation 812) the NDE report (i.e. inspection report) based on results of NDE analysis processing. An NDE report may be output for presentation, for example, through a GUI of an NDE application/service. In other examples, output of an NDE report may comprise transmitting the NDE report to a computing device and/or distributed data storage for user access.

Figure 9:
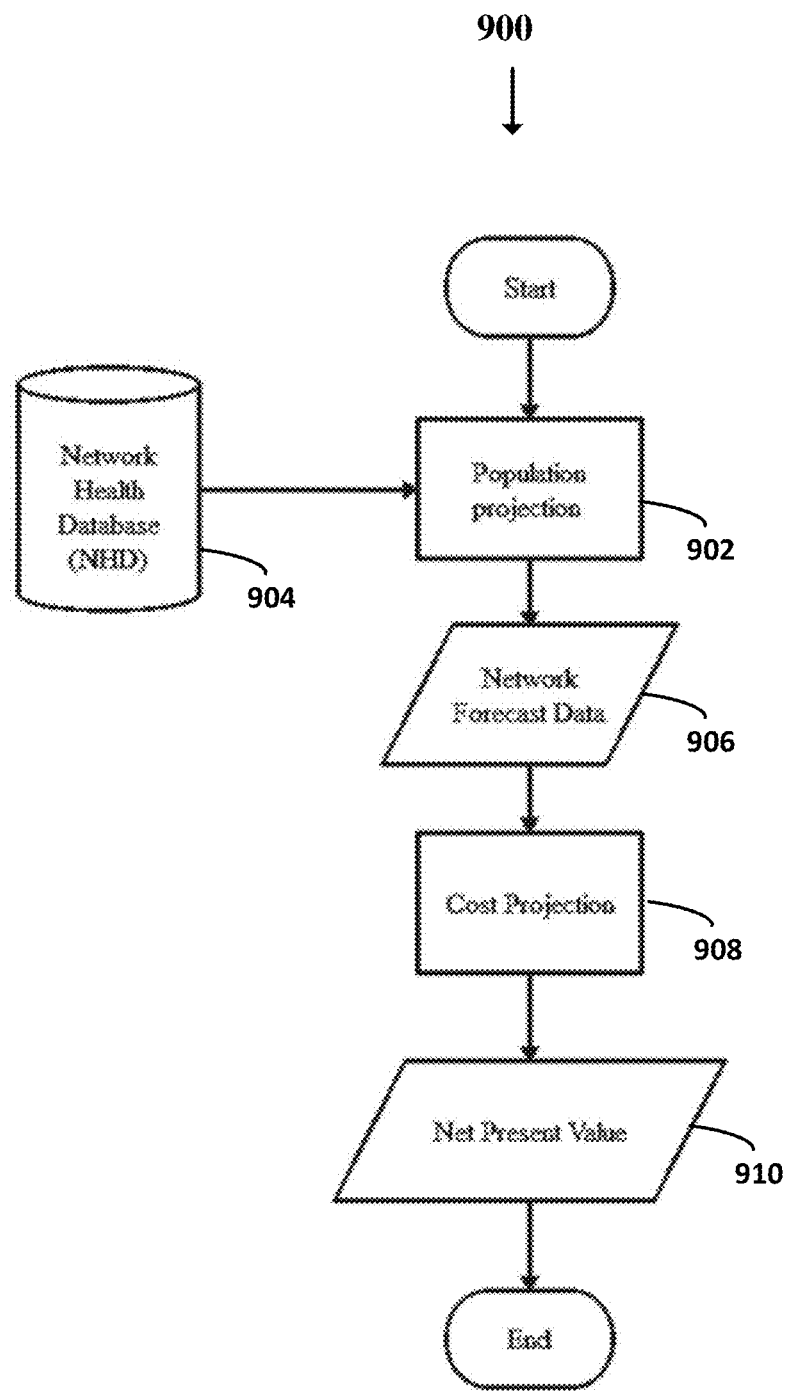
FIG. 9 illustrates a flow diagram highlighting network health analysis for NDE evaluation of a plurality of wooden specimen, with which aspects of the present disclosure may be practiced.

FIG. 9 illustrates a flow diagram 900 highlighting network health analysis for NDE evaluation of a plurality of wooden specimen, with which aspects of the present disclosure may be practiced. Examples of network health analysis for NDE evaluation of a plurality of wooden specimen (e.g., network of wooden specimen) have been described in the foregoing description.

The network health analysis segment statistically infers an entire network condition for wooden specimen based on the performed inspection results of a wooden specimen. As identified in the foregoing description, inspection results of a wooden specimen may be stored in a database of inspection analysis results. As identified in the description of FIG. 8, inspection results for NDE processing may be catalogued and stored. A network health assessment of a network of wooden specimen may be updated when additional rounds of NDE processing are performed (e.g., over a given time period such as yearly, every decade, etc.), which may impact an overall network health assessment for a network of wooden specimen.

Flow of flow diagram 900 begins at processing operation 902, where a population projection routine is executed. An implemented classifier may be trained to execute processing described herein resulting in execution of a population projection routine. Data regarding inspection of a specific network of wooden specimen may be identified from a database of inspection results for wooden specimen 904 (labeled as network health database (NHD) in flow diagram 900). Processing operation 902 comprises filtering the database of inspection results for wooden specimen 904 to identify data specific to a particular network of wooden specimen. This may comprise filtering out other inspection results that are not associated with a specific network of wooden specimen. Results specific to a network of wooden specimen may further be parsed to identify relevant data from inspection results and comparative analysis.

At processing operation 906, the population project routine applies A.I. based projection models on the filtered (and parsed) results data to predict future repairs and replacement activities required to maintain the structural integrity (e.g., condition and quality of the wooden specimen) of a network of wooden specimen. Additionally, processing operation 906 may comprise network forecast data details related to the aging profile of the network. This may comprise estimating aging and/or decay of a wooden specimen based on analysis of present conditions associated with the wooden specimen as well as investigation of historical data/pattern data for wooden specimen experiencing similar load and/or environmental conditions. The forecast data is then fed to the economic projection routine.

Flow of flow diagram 900 proceeds to processing operation 908, where an economic projection routine utilizes an economic model to estimate the net present value of the network of wooden specimen. This may comprise determining (processing operation 910) a net present value of the network of wooden specimen based on results of the analysis of various wooden specimen in the network of wooden specimen and/or historical patterns associated with similar wooden specimen as identified from data modeling analysis. In additional examples, a future budget profile (e.g., estimated future value) of the network of wooden specimen may also be generated in order to help a network manager of the network of wooden specimen to make informative funding decisions for network sustainment. This may comprise forecasting a future value of the network of wooden specimen based on results of the analysis of various wooden specimen in the network of wooden specimen and/or historical patterns associated with similar wooden specimen as identified from data modeling analysis. Results of said processing may be stored and/or output for inclusion in an NDE report.

FIGS. 10-18 illustrate processing device views of an NDE application/service usable to conduct NDE of a wooden specimen, with which aspects of the present disclosure may be practiced. Specific description of a GUI of an NDE application/service as well as features presented in a customized GUI have been described in the foregoing description. FIGS. 10-18 provide visual identification of non-limiting examples of a GUI and associated features that may be utilized to aid NDE processing as described in the present disclosure.

FIG. 10 illustrates processing device view 1000 providing a screenshot illustrating a GUI from an executing NDE application/service. Processing device view 1000 provides data indicating a connection of NDE devices with an NDE application/service that is executing on a computing device as described in the foregoing description. For instance, GUI of the NDE application/service may be configured to identify NDE devices and states of the NDE devices that are detected by an NDE application/service and present such data in the GUI for user viewing. Additional non-limiting examples of functionality that may also be presented through the GUI comprises features related to: management of a connection with NDE devices (e.g., testing and configuration of NDE devices); management of battery levels of NDE devices; initiation and management of signal feasibility testing; and initiation of NDE analysis, among other examples. As shown in processing device view 1000, the GUI may also be configured with user interface data fields that enable entry of testing parameters for NDE of a wooden specimen. In some examples, the GUI is configured to enable users to manually enter testing parameters. In other examples, some of the testing parameters may be automatically populated on behalf of a user based on execution of processing operations described herein.

Figure 11:
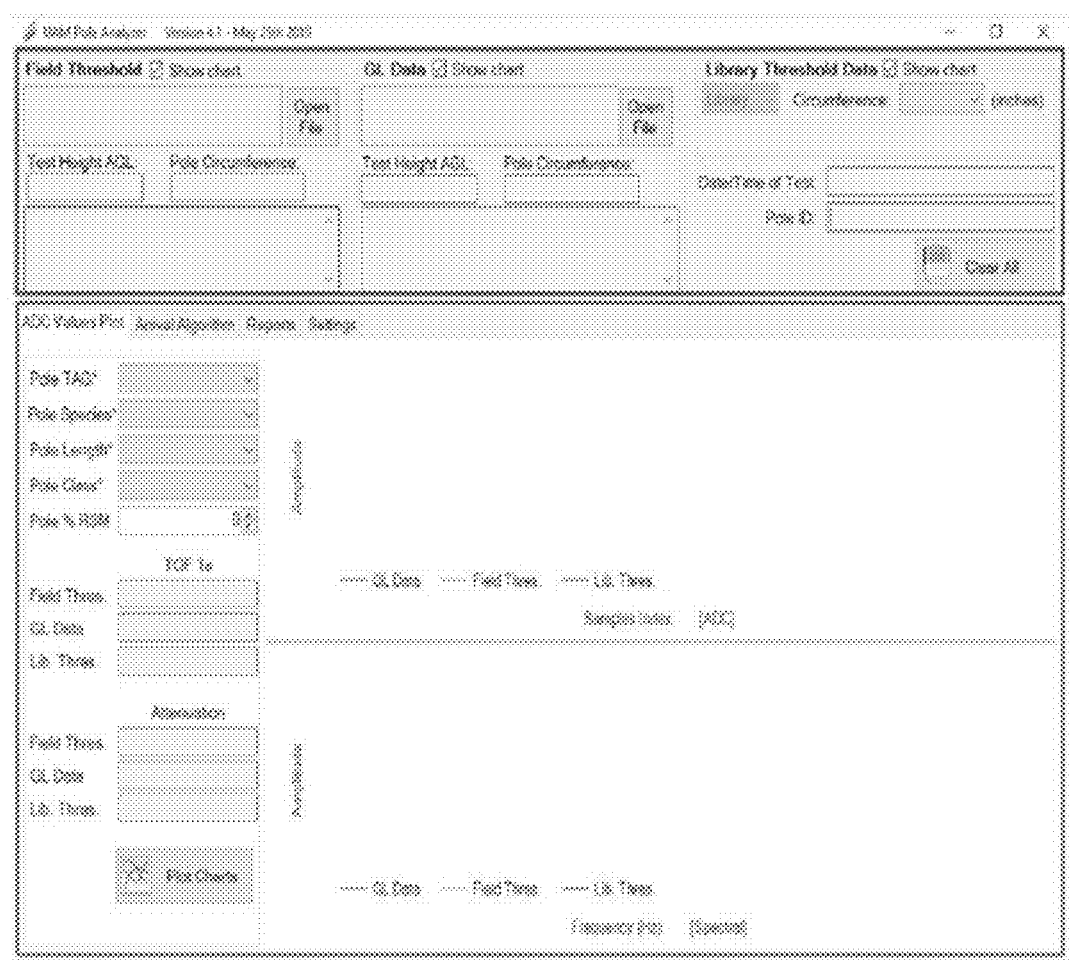

FIG. 11 illustrates processing device view 1100 providing a screenshot illustrating a GUI from an executing NDE application/service. Processing device view 1100 provides another example of entry of testing parameters through a GUI of an NDE application/service that enables NDE processing of a wooden specimen as described herein. At the top of processing device view 1100, data entry fields are provided that are related to a source selection menu. The source selection menu is configured to enable a user to enter source file data to aid NDE analysis of a wooden specimen. For instance, a user may select applicable sources (e.g., field/manual threshold; GL threshold, library threshold) as well as identify associated data files that an NDE application/service can utilize to execute its processing. Data files associated with thresholds may contain measured acoustic waveform data that can be used for comparison purposes. For example, a source file for a field threshold may be ultrasonic signal data received through interfacing with an NDE device or a saved data file from a previous instance of signal transmission while a source file for a library threshold may a source file retrieved from a database of inspection results that correlates with a specific type of wooden specimen being evaluated, among non-limiting examples. As an example, library threshold data allows the user to use a reference specimen with the same circumference from the library database, for example, when the manual threshold waveform signal is difficult to obtain.

As identified in the foregoing description, one or more regions of a wooden specimen may be identified for analytical purposes. This includes any regions of a wooden specimen including a GL and/or one or more other regions as a manual threshold/field threshold. In some examples, a field threshold is the GL. In further examples, data associated with a library threshold is usable to assist with pattern classification of ultrasonic signal data that is being evaluated. However, in some instances, a trained classifier may not require library data to classify a condition of a wooden specimen. In one instance, a field threshold other than the GL may be compared with a GL threshold to generate a classification of a wooden specimen, where major variations in waveform data at one of those testing points may be an indicator of incipient decay.

By clicking an "open file" button (shown in processing device view 1100), the GUI may be configured to present a dialog appears allowing the user to select data files containing waveform data for identified thresholds from a system file directory of a computing device that is executing the NDE application/service. Once the data files for selected thresholds are selected, the corresponding test height above the ground line (AGL), pole circumference and other attributes information is populated in the data entry fields from data retrieved from associated data files.

Figure 12:
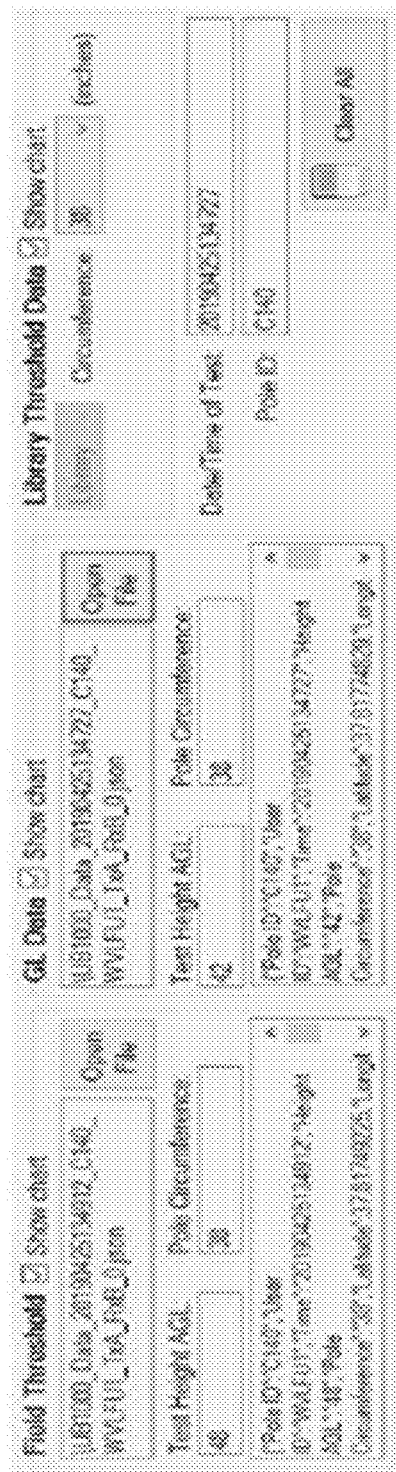

FIG. 12 illustrates processing device view 1200 providing a screenshot illustrating a GUI from an executing NDE application/service. Processing device view 1200 provides a continuation screenshot of the GUI where parameters of data fields described in processing device view 1100 (FIG. 11) are populated based on previously described processing. As shown in processing device view 1200, data fields in the GUI may be manually editable by a user. For instance, the NDE application/service may be configured to provide GUI features that enable users to adjust/reset testing parameters such as a "clear all" feature that may remove source file data.

Figure 13:
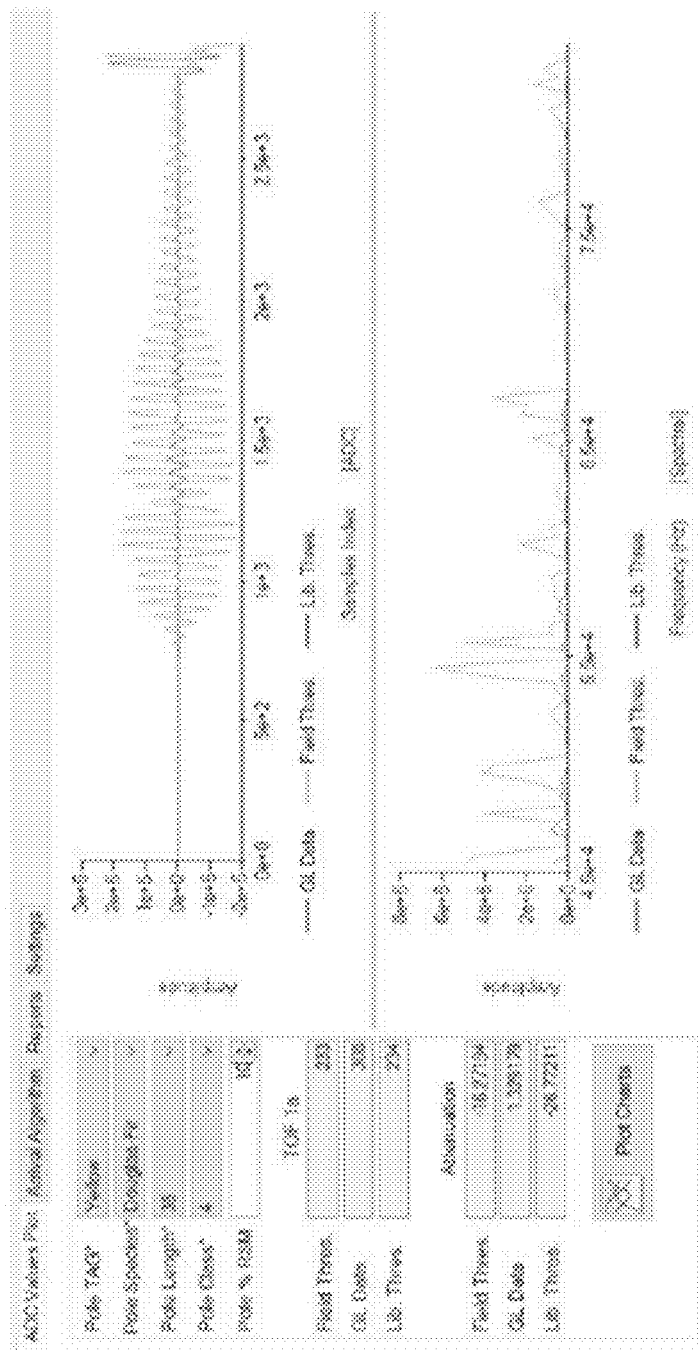

FIG. 13 illustrates processing device view 1300 providing a screenshot illustrating a GUI from an executing NDE application/service. Processing device view 1300 provides a non-limiting example of GUI of the NDE application/service where an analog-to-digital conversion (ADC) plot of acoustic signal data may be provided through a tab of the GUI. The GUI of the NDE application/service may be configured to enable users to select different tabs in the GUI, which provide different functionality. Some non-limiting examples of tabs are shown in FIGS. 13-18.

The ADC value plot contains two main plotting functions. They are the time domain plot and the frequency domain plot. The time domain plot displays a waveform of a received acoustic signal. When the field threshold and GL data are selected, the plot can display both signals simultaneously. The plot below represents the spectral graph displaying the energy levels of various frequencies from 45 kHz to 80 kHz. Other inspection information about the sample wooden specimen includes but is not limited to: specimen tag/identifier, species, length, class, quality of the wooden specimen and remaining strength modulus (RSM), among other examples. These attributes can be entered through a drop-down menu to the left of the plotting windows. The TOF group data fields display the corresponding TOF values of the different source data. Below it, the attenuation group data fields show the SNR signal of the different signals. By clicking the Plot Charts button, the NDE application/service is configured to populates the described plots and fields. Plots and data fields described herein may be included in a generated NDE report.

Figure 14:
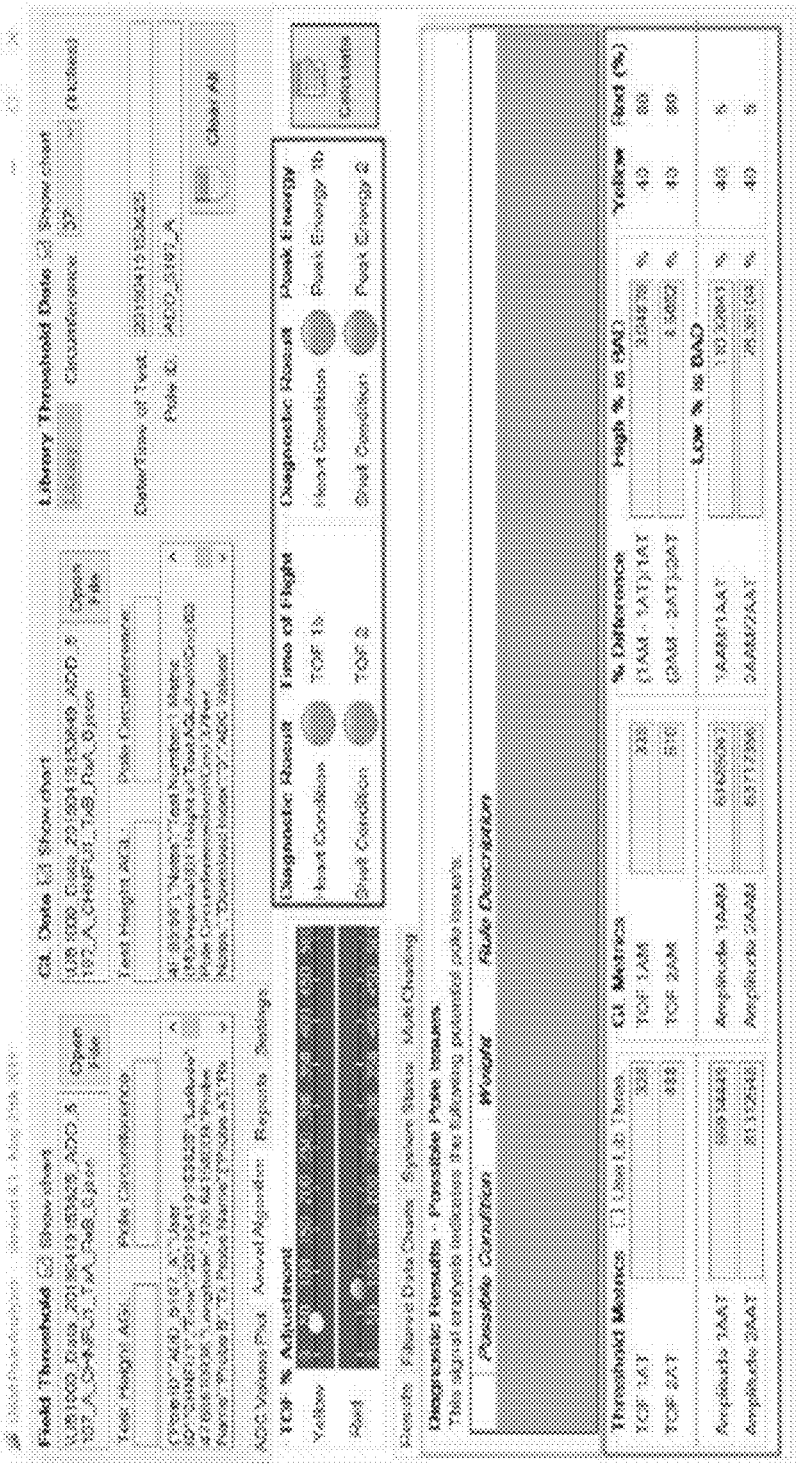
Figure 15:
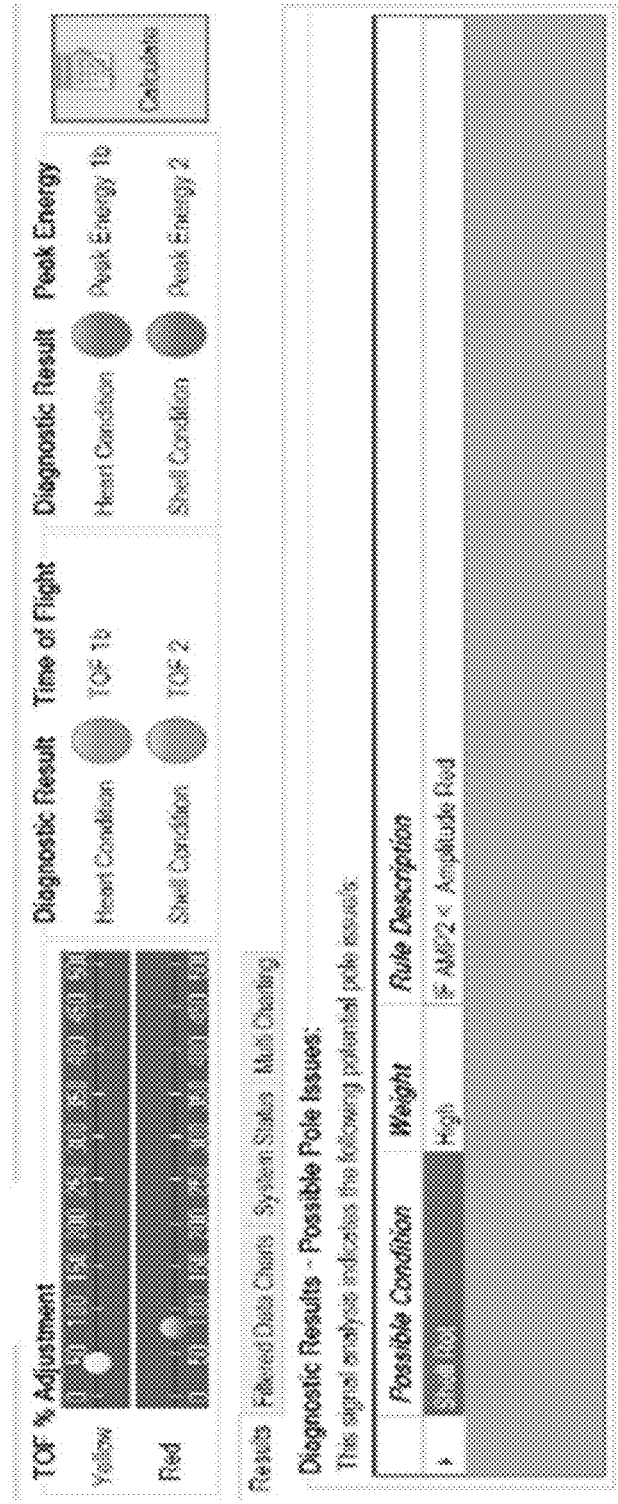

FIG. 14 illustrates processing device view 1400 providing a screenshot illustrating a GUI from an executing NDE application/service. Processing device view 1400 provides a non-limiting example of GUI of the NDE application/service where NDE analysis has been performed and results are reported through the GUI. FIGS. 14 and 15 illustrate different displays of another configured tab of the GUI, an arrival algorithm tab. A user may select the arrival algorithm tab to access specific analysis data regarding acoustic signal data from NDE analysis.

In the example shown in processing device view 1400, a user may select the "calculate button" from the GUI. By clicking the calculate button, the NDE application/service is configured to execute analysis of a received acoustic signal. The GUI may be configured to provide a condition indicator that is visually indicative of a classified condition and/or quality of a wooden specimen. As an example, the diagnostic result of the condition of the wooden specimen is categorized into the heart and shell regions. For each region, the TOFs and peak energy conditions are indicated using labels that may be color-coded for visual effect. For instance, as a non-limiting example, three different color indicators (e.g., green, yellow and red) may be utilized where green denotes the specimen has passed the inspection, yellow denotes the specimen marginal passed and may require further inspection and red denotes the specimen has failed the inspection. If a condition indicator shows a color other than green, the diagnostic results-possible pole issues text field may automatically be populated with a further explanation about the assessment result. Additional analytical analysis details may also be displayed as shown in processing device view 1400 to provide more in-depth understanding of the analysis. It is to be understood that any aspect of analysis may be provided through the GUI without departing from the spirit of the present disclosure.

FIG. 15 illustrates processing device view 1500 providing a screenshot illustrating a GUI from an executing NDE application/service. Processing device view 1500 provides a non-limiting example of GUI of the NDE application/service, where an alternative analysis result is provided through an exemplary arrival algorithm tab. Processing device view 1500 shows an assessment result of wooden specimen (e.g., wooden utility pole) having significant energy attenuations in both the heart and shell regions. A detail explanation is shown in a data field below the results. Additionally, the GUI may provide indication of a location where the calculated metrics are displayed (i.e., regions experiencing decay) as well more specific insights into why a specific classification was selected. The threshold metrics contain the calculated TOF values (TOF 1AT and TOF2AT denoting the TOF for the $1^{st}$ and $2^{nd}$ arrival). The energy information is represented in terms of the amplitude values denoted as 1AAT and 2AAT. Similarly, GL metrics contain the computed TOF1AM and TOF2AM with the energy values displayed as 1AAM and 2AAM. The relative differences between the TOF and energy levels with respect to the selected reference signal are shown to the right of processing device view 1500.

Figure 16:
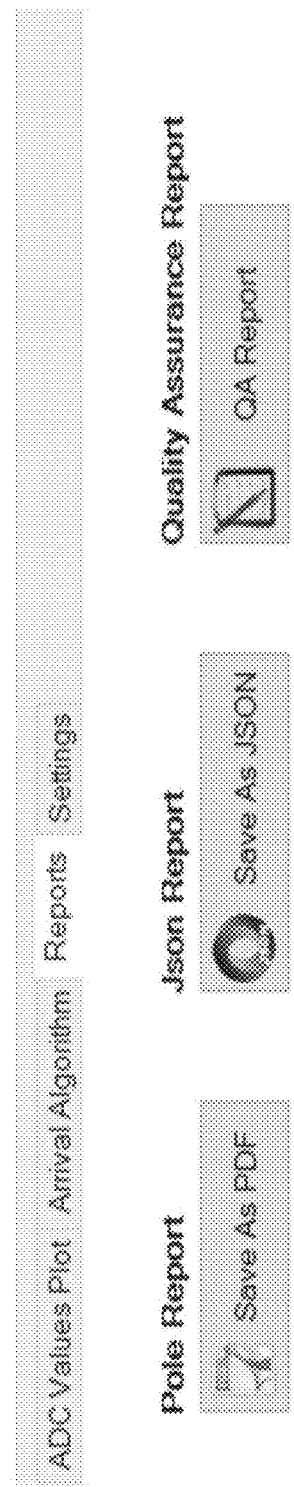

FIG. 16 illustrates processing device view 1600 providing a screenshot illustrating a GUI from an executing NDE application/service. Processing device view 1600 provides a non-limiting example of GUI of the NDE application/service, where a user can select a format for saving inspection results. That is, the GUI is configured to enable users to select a format of an NDE report that is generated for NDE analysis of one or more wooden specimen. In the example shown in processing device view 1600, an inspection result from the arrival calculations can be saved in three different non-limiting examples of file formats (e.g., PDF, JSON and Excel Spreadsheet formats). Once, a desired file format button is selected, the GUI may be configured to present a dialog allowing the user to choose preferred file directory to save a version of an NDE report.

Figure 17:

FIG. 17 illustrates processing device view 1700 providing a screenshot illustrating a GUI from an executing NDE application/service. Processing device view 1700 provides a non-limiting example of GUI of the NDE application/service, where a settings tab is displayed. The settings tab enables users to customize specific parameters for NDE analysis of a wooden specimen. Processing device view 1700 provides some non-limiting examples of parameters than can be configured to control NDE analysis of a wooden specimen. As previously referenced, and shown in processing device view 1700, source directories for waveform data that is utilized during NDE analysis can be adjusted. Furthermore, pass/fail criteria for processing described herein can modified such as that for signal feasibility testing. Additionally, rules and other variables for NDE analysis and classification determination can be adjusted in the settings tab. Examples of values that may be adjusted comprise but are not limited to: TOF parameters; attenuation value parameters; scientific parameters to evaluate for identifying peak energy; and rules for determining a classification of a condition of a wooden specimen, among other non-limiting examples. Looking deeper at parameters that may be modified include a weighting that is applied to certain conditions/defects that may be detected during analysis of a wooden specimen. Data modeling may operate to adjust a classification determination based on specific conditions/defects detected for a wooden specimen, for example, that may be weighed more heavily in a specific technical analysis. Examples of such conditions/defects comprise but are not limited to: heart rot; shell rot; shell separation; and detection of high moisture content, among other non-limiting examples. An exemplary GUI may further comprise selectable user interface features to help users apply changes for NDE analysis of a wooden specimen.

Figure 18:
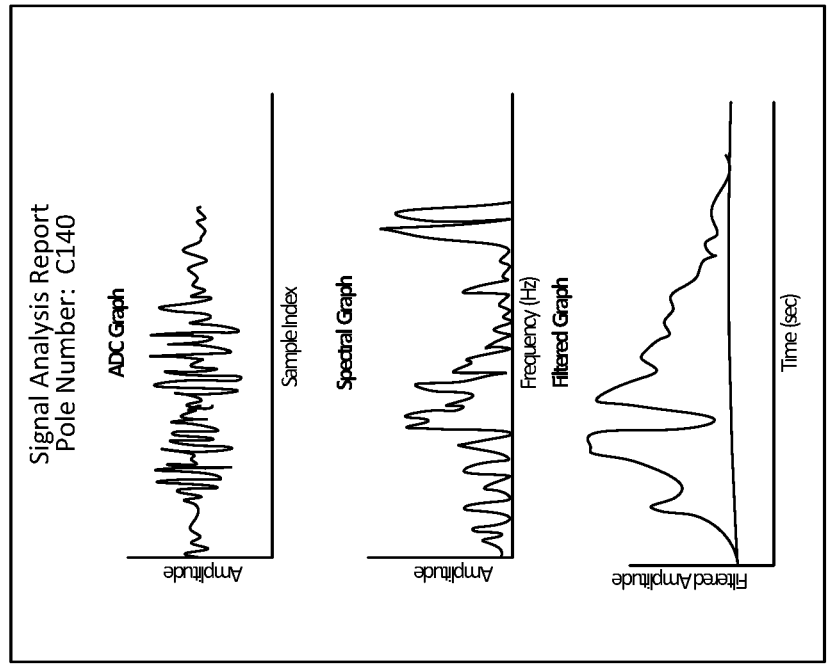
Figure 18:
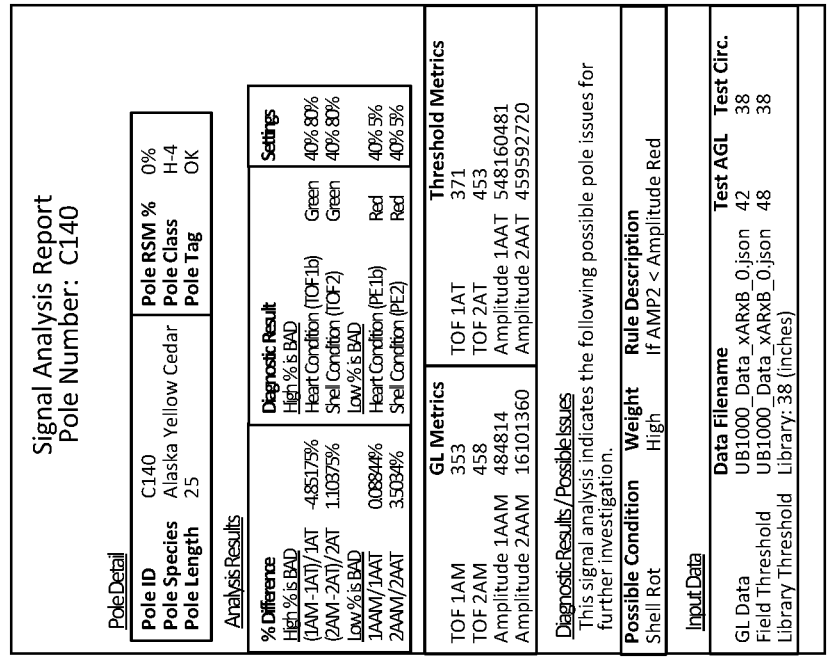

FIG. 18 illustrates processing device view 1800 providing a screenshot illustrating a GUI from an executing NDE application/service. Processing device view 1800 provides a non-limiting example of GUI of the NDE application/service where an exemplary NDE report is generated and presented. In one example, the NDE report may be displayed in a GUI of the NDE application/service. In further examples, an NDE report may be launched in a native application/service of a data format that is selected for displaying the NDE report. For instance, if a user selects a PDF format for display of an NDE report, a PDF reader may be launched to display the NDE report. As referenced in the foregoing description, an NDE report may provide a comprehensive analysis of results from NDE processing. However, in some examples, NDE reports may be customized to include a subset of the available reporting features at the discretion of a user.

Figure 19:
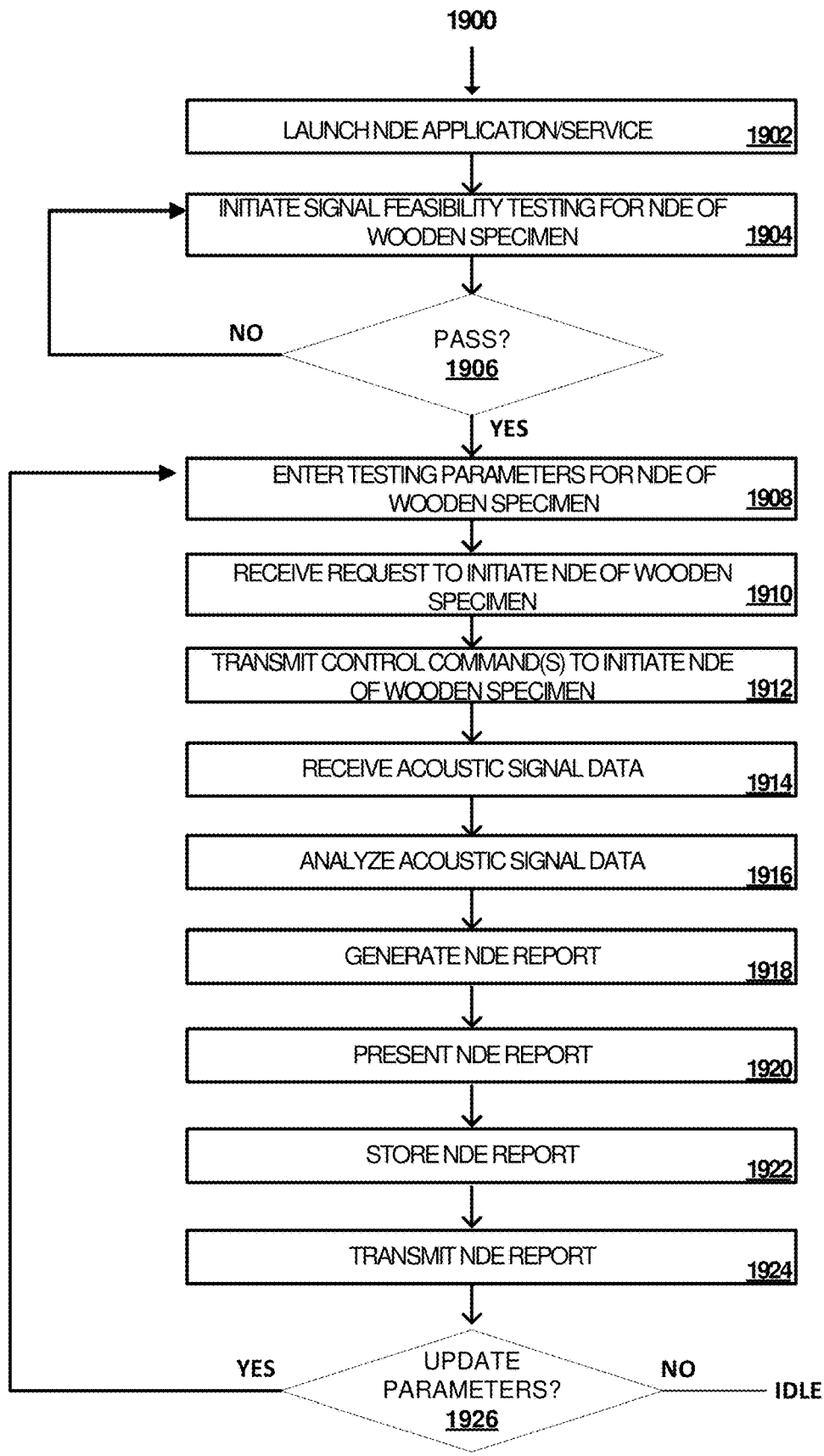
FIG. 19 illustrates an exemplary method for execution of NDE of a wooden specimen through an exemplary NDE application/service, with which aspects of the present disclosure may be practiced.

FIG. 19 illustrates an exemplary method 1900 for execution of NDE of a wooden specimen through an exemplary NDE application/service, with which aspects of the present disclosure may be practiced. As an example, method 1900 may be executed on an exemplary computing system 2001 (or across multiple computing systems) as described in the description of FIG. 20. Exemplary components, described in method 1900, may be hardware and/or software components, which are programmed to execute processing operations described herein. Operations performed in method 1900 may correspond to operations executed by a system and/or service that execute computer programs, software agents, intelligent bots, application programming interfaces (APIs), artificial intelligence (AI) such as machine learning processing and/or deep learning data modeling, neural networks, etc., among other examples. In some examples, processing operations described in method 1900 may be executed by one or more applications/services associated with a web service that has access to a plurality of application/services, devices, knowledge resources, etc. For example, an NDE application/service may be programmed to execute processing operations described herein while interfacing with a plurality of other resources (e.g., databases, file repositories, applications/services) to accomplish processing described herein. In one instance, processing operations described in method 1900 may be implemented by one or more components connected over a distributed network.

Method 1900 begins at processing operation 1902, where an NDE application/service is launched. The NDE application/service may be launched on a computing device, for example, that is configured to interface with one or more NDE devices via a data transmission connection to conduct NDE processing of a wooden specimen. Examples of an NDE application/service have been provided in the foregoing description.

Flow may proceed to processing operation 1904, where signal feasibility testing is initiated to confirm that NDE processing can proceed to properly evaluate one or more regions of a wooden specimen. Examples of signal feasibility processing have been provided in the foregoing description. Results of signal feasibility testing may be evaluated.

At decision operation 1906, it is determined whether signal feasibility requirements are satisfied. In examples where signal feasibility testing requirements are not satisfied, flow of decision operation 1906 branches NO and processing of method 1900 may end (or restart once parameters have been modified). In examples where signal feasibility testing requirements are satisfied, flow of decision operation 1906 branches YES and NDE processing proceeds.

Method 1900 may proceed to processing operation 1908, where testing parameters for NDE of a wooden specimen are entered through a GUI of an NDE application/service. The GUI enables users to enter customized testing parameters that may relate to a specific testing scenario. Examples of parameters that may be entered comprise but are not limited to: testing identification data (e.g., name, date, location, identifying tags, inspector identification); physical characteristics of the wooden specimen (including physical dimensions); load conditions affecting the wooden specimen; environmental conditions associated with the wooden specimen; variables and rules for data modeling analysis; source files for collecting/accessing acoustic signal data for analytical evaluation; and other associated settings as described herein, among other examples.

Once testing parameters have been identified and entered, flow of method 1900 may proceed to processing operation 1910, where NDE analysis processing is initiated. In processing operation 1910, a user interface selection may be received through a GUI to initiate analysis processing. Receipt of an indication to initiate NDE analysis processing results in method 1900 proceeding to processing operation 1912. At processing operation 1912, the computing device, executing the NDE application/service, is configured to transmit one or more control commands to one or more NDE devices to initiate NDE of a wooden specimen. An exemplary control command may trigger initiation of ultrasonic signal transmission via an NDE device as well as prepare an NDE device for receipt of acoustic signal data transmitted through and around the wooden specimen. Results from transmission of acoustic signal(s) through a wooden specimen may be received (processing operation 1914) from one or more NDE devices to the computing device to initiate NDE processing by the NDE application/service.

Flow of method 1900 may proceed to processing operation 1916, where acoustic signal data, received at the computing device, is analyzed. As described in the foregoing, an exemplary NDE application/service is configured to analyze captured acoustic signal data (e.g., ultrasonic signal data) and transform that captured signal data into relevant feature information that is used to accurately assess the structural integrity (e.g., condition and quality) of a specimen (e.g., wooden specimen). Analysis of acoustic signal data (i.e. waveforms thereof) combines time of flight (TOF) and energy attenuation information (e.g., peak energy of a waveform) to qualitatively determine mechanical moduli that are directly related to material strength. For instance, execution of a programmed NDE application/service employs a trained artificial intelligence (AI) classifier that evaluates waveform propagation (e.g., TOF and energy attenuation) through a wooden specimen to classify condition and remaining strength of the wooden specimen. A classification of a structural integrity of a wooden specimen may be included in an NDE report that is generated and surfaced, for example, through the graphical user interface of the NDE application/service or an application/service that is associated with a selected format of the NDE report as identified in the graphical user interface. In further examples, the trained AI classifier may be further configured to contemplate other factors associated with a wooden specimen such as load conditions, environmental conditions, physical conditions, etc. This enables a more comprehensive NDE report to be generated that may pertain to the state of a wooden specimen and/or a network of wooden specimen. That is, an NDE report may reflect a present state of one or more wooden specimen, a projected future state of one or more wooden specimen or a combination thereof.

Method 1900 may proceed to processing operation 1918, where an NDE report is generated. Processing for generation (processing operation 1918) of an NDE report has been described in the foregoing description. A generated NDE report may be presented (processing operation 1920) via a computing device that is executing the NDE application/service. In one example, presentation (processing operation 1920) of an NDE report may comprise presenting the NDE report through a GUI of the NDE application/service. In another example, presentation (processing operation 1920) of an NDE report may comprise launching an application/service that is associated with a format of an NDE report that is selected through the GUI of the NDE application/service and displaying the NDE report in that launched application/service.

At processing operation 1922, the NDE report may be stored. In some examples, an NDE report may be stored on a computing device in which the NDE report was generated. In other examples, an NDE report may be transmitted (processing operation 1924) to another device or a distributed storage (e.g., cloud-based storage). For instance, the NDE application/service may be configured to generate an NDE report and transmit (processing operation 1924) the NDE report to a database or email server of a user, among other non-limiting examples.

After NDE processing has completed, flow may proceed to decision operation 1926, where it is determined whether there is an update to parameters associated with NDE processing. In examples where no update occurs, flow of decision operation 1926 may branch NO and processing of method 1900 remains idle (or ends) until subsequent NDE processing resumes. In examples where an update occurs to parameters associated with the NDE processing, flow of decision operation 1926 branches YES, and processing of method 1900 may return to processing operation 1908. At that junction, testing parameters may be updated and NDE processing may be re-initiated.

Figure 20:
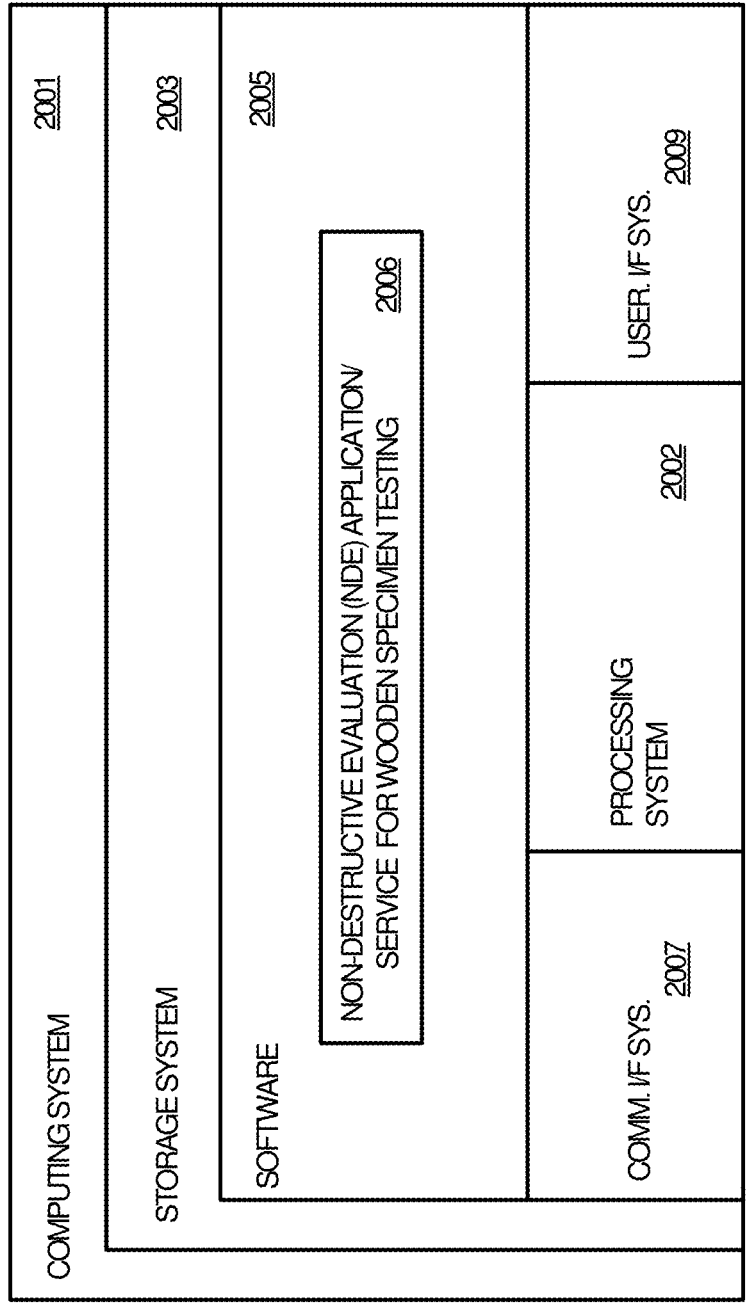
FIG. 20 illustrates a computing system suitable for implementing processing operations described herein related to NDE of a wooden specimen, with which aspects of the present disclosure may be practiced.

FIG. 20 illustrates a computing system 2001 suitable for implementing processing operations described herein related to NDE of a wooden specimen, with which aspects of the present disclosure may be practiced. Computing system 2001 may be implemented as a single apparatus, system, or device or may be implemented in a distributed manner as multiple apparatuses, systems, or devices. For example, computing system 2001 may comprise one or more computing devices that execute processing for applications and/or services over a distributed network to enable execution of processing operations described herein over one or more services. Computing system 2001 comprises, but is not limited to, processing system 2002, storage system 2003, software 2005, communication interface system 2007, and user interface system 2009. Processing system 2002 is operatively coupled with storage system 2003, communication interface system 2007, and user interface system 2009. Non-limiting examples of computer system 2001 comprise but are not limited to: smart phones, laptops, tablets, PDAs, desktop computers, servers, smart computing devices including television devices and wearable computing devices, e-reader devices, and conferencing systems, among other non-limiting examples. Other types of processing devices may be utilized as computer system 2001 without departing from the spirit of the present disclosure.

Processing system 2002 loads and executes software 2005 from storage system 2003. Software 2005 includes one or more software components 2006 that execute an NDE application/service for testing of a wooden specimen. In some examples, computing system 2001 may be a device that a user utilizes to interface with an NDE device via the NDE application/service for wooden specimen testing 2006. For example, computing device 2001, through execution of the NDE application/service for wooden specimen testing 2006, interfaces with an NDE device via a data transmission component of the NDE device where commands may be sent and signal data can be received. The computing device 2001 may interface with an NDE device via wired connection or wireless connection including any data transmission protocols as known to one skilled in the field of art. When executed by processing system 2002, software 2005 directs processing system 2002 to operate as described herein for at least the various processes, operational scenarios, and sequences discussed in the foregoing implementations. Computing system 2001 may optionally include additional devices, features, or functionality not discussed for purposes of brevity.

Computing system 2001 may further be utilized to control operation of NDE devices, for example, where a mode of operation of an NDE device may be managed through an exemplary NDE application/service executing on computing system 2001. For instance, a GUI of an NDE application/service may be configured to present user interface elements that enable users to toggle modes of operation of an NDE device that interface with computing system 2001. Examples of modes of operation of an NDE device comprise but are not limited to: a standby mode; a transmitting mode; a receiving mode; and a hybrid transmitting/receiving mode, among other examples. In instances where a computing system 2001 is transmitting commands to set an NDE device in one of the above-identified modes, commands may be transmitted to a processing unit of an NDE device that is configured to receive such commands via a data transmission component of the NDE device. As such, a computing device 2001 may be configured to implement a data transmission component that works with a same data transmission protocol that an NDE device is configured to receive data through. Moreover, computing system 2001 may further be configured to enable control parameters related to any aspect of NDE of wooden specimen, for example, through a GUI of an NDE application/service. This comprises but is not limited to: configuration of NDE devices; management of signal feasibility testing; management of parameters for NDE of wooden specimen; management and training of data modeling to assist with NDE analysis of acoustic signal data; network health analysis of a sample population of wooden specimen; generation of NDE reports including generation of customized NDE reports; and management of NDE reports (e.g., storage and transmission), among other examples.

Referring still to FIG. 20, processing system 2002 may comprise processor, a micro-processor and other circuitry that retrieves and executes software 2005 from storage system 2003. Processing system 2002 may be implemented within a single processing device but may also be distributed across multiple processing devices or sub-systems that cooperate in executing program instructions. Examples of processing system 2002 include general purpose central processing units, microprocessors, graphical processing units, application specific processors, sound cards, speakers and logic devices, as well as any other type of processing devices, combinations, or variations thereof.

Storage system 2003 may comprise any computer readable storage media readable by processing system 2002 and capable of storing software 2005. Storage system 2003 may include volatile and nonvolatile, removable and non-removable media implemented in any method or technology for storage of information, such as computer readable instructions, data structures, program modules, cache memory or other data. Examples of storage media include random access memory, read only memory, magnetic disks, optical disks, flash memory, virtual memory and non-virtual memory, magnetic cassettes, magnetic tape, magnetic disk storage or other magnetic storage devices, or other suitable storage media, except for propagated signals. In no case is the computer readable storage media a propagated signal.

In addition to computer readable storage media, in some implementations storage system 2003 may also include computer readable communication media over which at least some of software 2005 may be communicated internally or externally. Storage system 2003 may be implemented as a single storage device but may also be implemented across multiple storage devices or sub-systems co-located or distributed relative to each other. Storage system 2003 may comprise additional elements, such as a controller, capable of communicating with processing system 2002 or possibly other systems. In some examples, storage system 2003 is a distributed network storage/web storage, where computing device 2001 is configured to connect to the distributed network storage/web storage via a network connection.

Software 2005 may be implemented in program instructions and among other functions may, when executed by processing system 2002, direct processing system 2002 to operate as described with respect to the various operational scenarios, sequences, and processes illustrated herein. For example, software 2005 may include program instructions for an NDE application/service for wooden specimen testing 2006, as described in the foregoing description.

In particular, the program instructions may include various components or modules that cooperate or otherwise interact to carry out the various processes and operational scenarios described herein. The various components or modules may be embodied in compiled or interpreted instructions, or in some other variation or combination of instructions. The various components or modules may be executed in a synchronous or asynchronous manner, serially or in parallel, in a single threaded environment or multi-threaded, or in accordance with any other suitable execution paradigm, variation, or combination thereof. Software 2005 may include additional processes, programs, or components, such as operating system software, virtual machine software, or other application software. Software 2005 may also comprise firmware or some other form of machine-readable processing instructions executable by processing system 2002.

In general, software 2005 may, when loaded into processing system 2002 and executed, transform a suitable apparatus, system, or device (of which computing system 2001 is representative) overall from a general-purpose computing system into a special-purpose computing system customized to process data and respond to queries. Indeed, encoding software 2005 on storage system 2003 may transform the physical structure of storage system 2003. The specific transformation of the physical structure may depend on various factors in different implementations of this description. Examples of such factors may include, but are not limited to, the technology used to implement the storage media of storage system 2003 and whether the computer-storage media are characterized as primary or secondary storage, as well as other factors.

For example, if the computer readable storage media are implemented as semiconductor-based memory, software 2005 may transform the physical state of the semiconductor memory when the program instructions are encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate the present discussion.

Communication interface system 2007 may include communication connections and devices that allow for communication with other computing systems (not shown) over communication networks (not shown). Communication interface system 2007 may also be utilized to cover interfacing between processing components described herein. Examples of connections and devices that together allow for inter-system communication may include network interface cards or devices, wired and/or wireless modules, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned media, connections, and devices are well known and need not be discussed at length here.

User interface system 2009 is optional and may include a keyboard, a mouse, a voice input device, a touch input device for receiving a touch gesture from a user, a motion input device for detecting non-touch gestures and other motions by a user, and other comparable input devices and associated processing elements capable of receiving user input from a user. Output devices such as a display, speakers, haptic devices, and other types of output devices may also be included in user interface system 2009. In some cases, the input and output devices may be combined in a single device, such as a display capable of displaying images and receiving touch gestures. The aforementioned user input and output devices are well known in the art and need not be discussed at length here.

User interface system 2009 may also include associated user interface software executable by processing system 2002 in support of the various user input and output devices discussed above. Separately or in conjunction with each other and other hardware and software elements, the user interface software and user interface devices may support a graphical user interface, a natural user interface, or any other type of user interface, for example, that enables front-end processing of exemplary application/services described herein (including an NDE application/service for wooden specimen testing 2006). A graphical user interface of user interface system 2009 may further be configured to display graphical user interface elements (e.g., data fields, menus, graphs, charts, data correlation representations and identifiers, control elements, real-time (or near real-time) testing data; waveform data, etc.) that are representations generated from processing ultrasonic signal data received from one or more NDE devices. For example, processing of received ultrasonic signal data, received from one or more NDE devices, may be utilized to provide explicit statistical data regarding a condition of a wooden specimen as well as classifications of a state of a wooden specimen that reflect algorithmic analysis of received ultrasonic signal data (e.g., that the wooden specimen is: tagged for replacement, flagged for re-testing at specified future time period; in good condition). Furthermore, as referenced above, data modeling of an exemplary NDE application/service is configured to enable projections to be provided for a wooden specimen (or a plurality of wooden specimen) where projections may relate to an estimated condition of a wooden specimen, recommendations for future management of wooden specimen and valuation of wooden specimen. As referenced in the foregoing description, valuation of wooden specimen, based on analysis provided herein, may comprise present valuations as well as future valuation projections. As referenced in the foregoing description, an exemplary GUI may further be configured to enable users to send control commands to control NDE of a wooden specimen. For example, commands may be transmitted to vary scientific parameters (e.g., voltage, resonance frequency) associated with NDE of a wooden specimen.

Communication between computing system 2001 and other computing systems (not shown), may occur over a communication network or networks and in accordance with various communication protocols, combinations of protocols, or variations thereof. Examples include intranets, internets, the Internet, local area networks, wide area networks, wireless networks, wired networks, virtual networks, software defined networks, data center buses, computing backplanes, or any other type of network, combination of network, or variation thereof. The aforementioned communication networks and protocols are well known and need not be discussed at length here. However, some communication protocols that may be used include, but are not limited to, the Internet protocol (IP, IPv4, IPv6, etc.), the transfer control protocol (TCP), and the user datagram protocol (UDP), Bluetooth, infrared, RF, cellular networks, satellite networks, global positioning systems, as well as any other suitable communication protocol, variation, or combination thereof.

In any of the aforementioned examples in which data, content, or any other type of information is exchanged, the exchange of information may occur in accordance with any of a variety of protocols, including FTP (file transfer protocol), HTTP (hypertext transfer protocol), REST (representational state transfer), WebSocket, DOM (Document Object Model), HTML (hypertext markup language), CSS (cascading style sheets), HTML5, XML (extensible markup language), JavaScript, JSON (JavaScript Object Notation), and AJAX (Asynchronous JavaScript and XML), as well as any other suitable protocol, variation, or combination thereof.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

Reference has been made throughout this specification to "one example" or "an example," meaning that a particular described feature, structure, or characteristic is included in at least one example. Thus, usage of such phrases may refer to more than just one example. Furthermore, the described features, structures, or characteristics may be combined in any suitable manner in one or more examples.

One skilled in the relevant art may recognize, however, that the examples may be practiced without one or more of the specific details, or with other methods, resources, materials, etc. In other instances, well known structures, resources, or operations have not been shown or described in detail merely to observe obscuring aspects of the examples.

While sample examples and applications have been illustrated and described, it is to be understood that the examples are not limited to the precise configuration and resources described above. Various modifications, changes, and variations apparent to those skilled in the art may be made in the arrangement, operation, and details of the methods and systems disclosed herein without departing from the scope of the claimed examples.

What is claimed is:

1. A method for non-destructive evaluation (NDE) of a wooden specimen, comprising:
    launching, on a computing device, a graphical user interface of an NDE application or service;
    receiving, through the graphical user interface, entry of testing parameters for NDE of one or more regions of the wooden specimen;
    receiving, through the graphical user interface, a request to initiate NDE of the one or more regions of the wooden specimen;
    in response to the received request to initiate NDE of the one or more regions of the wooden specimen, receiving acoustic signal data for NDE of the one or more regions of the wooden specimen;
    analyzing the received acoustic signal data to extract features that correspond with one or more regions of the wooden specimen;
    generating an NDE report that comprises a classification of a structural integrity of the wooden specimen based on the analyzing of the received acoustic signal data; and
    presenting the generated NDE report.

2. The method of claim 1, wherein the analyzing of the received acoustic signal data further comprises executing data modeling that utilizes a trained classifier to determine the classification of the structural integrity of the wooden specimen based on evaluation of the extracted features that correspond with the one or more regions of the wooden specimen.

3. The method of claim 2, wherein the analyzing comprises extracting, from a waveform of the acoustic signal data, time of flight (TOF) data and peak energy data associated with the one or more regions of the wooden specimen, and wherein the trained classifier utilizes the TOF data and the peak energy data to determine the classification of the structural integrity of the wooden specimen.

4. The method of claim 1, wherein the entry of testing parameters comprises an identification of one or more source files indicating specific data sources usable for comparative waveform analysis to determine the classification of the structural integrity of the wooden specimen, and wherein the one or more source files are selected from a group that comprises: a field threshold corresponding to the one or more regions of the wooden specimen; a ground line threshold corresponding with a ground line of the wooden specimen; and a library threshold corresponding with reference specimen obtained from a library database.

5. The method of claim 1, wherein the entry of testing parameters comprises receiving, through the user interface, entry of one or more selected from a group that comprises: physical characteristics of the wooden specimen; load conditions affecting the wooden specimen; and environmental conditions associated with the wooden specimen.

6. The method of claim 1, further comprising: initiating, through the graphical user interface, signal feasibility testing of an NDE device; receiving results of the signal feasibility testing through the graphical user interface; and presenting, through the graphical user interface, the results of the signal feasibility testing.

7. The method of claim 1, further comprising: receiving, through the graphical user interface, adjustment of the testing parameters; and initiating, through the graphical user interface, subsequent NDE of the one or more regions of the wooden specimen based on the adjustment of the testing parameters.

8. A computing device comprising:
one or more computer-readable storage media;
one or more processors operatively coupled with the one or more computer-readable storage media; and
an application for performing non-destructive evaluation (NDE) of a wooden specimen comprising program instructions stored on the one or more computer-readable storage media that, when executed by the one or more processors, direct the computing device to at least:
launch, on the computing device, a graphical user interface of the application;
receive, through the graphical user interface, entry of testing parameters for NDE of one or more regions of the wooden specimen;
receive, through the graphical user interface, a request to initiate NDE of the one or more regions of the wooden specimen;
in response to the received request to initiate NDE of the one or more regions of the wooden specimen, receive acoustic signal data for NDE of the one or more regions of the wooden specimen;
analyze the received acoustic signal data to extract features that correspond with one or more regions of the wooden specimen;
generate an NDE report that comprises a classification of a structural integrity of the wooden specimen based on the analyzing of the received acoustic signal data; and
present the generated NDE report.

9. The computing device of claim 8, wherein to analyze the received acoustic signal data, the program instructions direct the computing device to execute data modeling that utilizes a trained classifier to determine the classification of the structural integrity of the wooden specimen based on evaluation of the extracted features that correspond with the one or more regions of the wooden specimen.

10. The computing device of claim 9, wherein to analyze the received acoustic signal data, the program instructions further direct the computing device to extract, from a waveform of the acoustic signal data, time of flight (TOF) data and peak energy data associated with the one or more regions of the wooden specimen, and wherein the trained classifier utilizes the TOF data and the peak energy data to determine the classification of the structural integrity of the wooden specimen.

11. The computing device of claim 8, wherein the entry of testing parameters comprises an identification of one or more source files indicating specific data sources usable for comparative waveform analysis to determine the classification of the structural integrity of the wooden specimen, wherein the one or more source files are selected from a group that comprises: a field threshold corresponding to the one or more regions of the wooden specimen, a ground line threshold corresponding with a ground line of the wooden specimen, and a library threshold corresponding with reference specimen obtained from a library database.

12. The computing device of claim 8, wherein to receive the entry of testing parameters, the program instructions direct the computing device to receive, through the graphical user interface, entry of one or more selected from a group that comprises: physical characteristics of the wooden specimen, load conditions affecting the wooden specimen, and environmental conditions associated with the wooden specimen.

13. The computing device of claim 8, wherein the program instructions further direct the computing device to:
initiate, through the graphical user interface, signal feasibility testing of an NDE device;
receive results of the signal feasibility testing through the graphical user interface; and
present, through the graphical user interface, the results of the signal feasibility testing.

14. The computing device of claim 8, wherein the program instructions further direct the computing device to:
receive, through the graphical user interface, adjustment of the testing parameters; and
initiate, through the graphical user interface, subsequent NDE of the one or more regions of the wooden specimen based on the adjustment of the testing parameters.

15. One or more computer-readable storage media having program instructions stored thereon that, when executed by one or more processors operatively coupled with the one or more computer-readable storage media, direct a computing apparatus to at least:
launch, on the computing apparatus, a graphical user interface of a non-destructive evaluation (NDE) application or service;
receive, through the graphical user interface, entry of testing parameters for NDE of one or more regions of the wooden specimen;
receive, through the graphical user interface, a request to initiate NDE of the one or more regions of the wooden specimen;
in response to the received request to initiate NDE of the one or more regions of the wooden specimen, receive acoustic signal data for NDE of the one or more regions of the wooden specimen;
analyze the received acoustic signal data to extract features that correspond with one or more regions of the wooden specimen;
generate an NDE report that comprises a classification of a structural integrity of the wooden specimen based on the analyzing of the received acoustic signal data; and
present the generated NDE report.

16. The one or more computer-readable storage media of claim 15, wherein to analyze the received acoustic signal data, the program instructions direct the computing apparatus to execute data modeling that utilizes a trained classifier to determine the classification of the structural integrity of the wooden specimen based on evaluation of the extracted features that correspond with the one or more regions of the wooden specimen.

17. The one or more computer-readable storage media of claim 16, wherein to analyze the received acoustic signal data, the program instructions further direct the computing apparatus to extract, from a waveform of the acoustic signal data, time of flight (TOF) data and peak energy data associated with the one or more regions of the wooden specimen, and wherein the trained classifier utilizes the TOF data and the peak energy data to determine the classification of the structural integrity of the wooden specimen.

18. The one or more computer-readable storage media of claim 15, wherein the entry of testing parameters comprises an identification of one or more source files indicating specific data sources usable for comparative waveform analysis to determine the classification of the structural integrity of the wooden specimen, and wherein the one or more source files are selected from a group that comprises: a field threshold corresponding to the one or more regions of the wooden specimen, a ground line threshold corresponding with a ground line of the wooden specimen, and a library threshold corresponding with reference specimen obtained from a library database.

19. The one or more computer-readable storage media of claim 15, wherein to receive the entry of testing parameters, the program instructions direct the computing apparatus to receive, through the graphical user interface, entry of one or more selected from a group that comprises: physical characteristics of the wooden specimen, load conditions affecting the wooden specimen, and environmental conditions associated with the wooden specimen.

20. The one or more computer-readable storage media of claim 15, wherein the program instructions further direct the computing apparatus to:
    initiate, through the graphical user interface, signal feasibility testing of an NDE device;
    receive results of the signal feasibility testing through the graphical user interface; and
    present, through the graphical user interface, the results of the signal feasibility testing.

21. The one or more computer-readable storage media of claim 15, wherein the program instructions further direct the computing apparatus to:
    receive, through the graphical user interface, adjustment of the testing parameters; and
    initiate, through the graphical user interface, subsequent NDE of the one or more regions of the wooden specimen based on the adjustment of the testing parameters.

* * * * *